US008097459B2

(12) United States Patent
Jin et al.

(10) Patent No.: US 8,097,459 B2
(45) Date of Patent: Jan. 17, 2012

(54) METHODS AND COMPOSITIONS FOR INCREASING REPLICATION CAPACITY OF AN INFLUENZA VIRUS

(75) Inventors: Hong Jin, Cupertino, CA (US); Bin Lu, Los Altos, CA (US)

(73) Assignee: Medimmune, LLC, Gaithersburg, MD (US)

( * ) Notice: Subject to any disclaimer, the term of this patent is extended or adjusted under 35 U.S.C. 154(b) by 88 days.

(21) Appl. No.: 12/552,018

(22) Filed: Sep. 1, 2009

(65) Prior Publication Data

US 2010/0062532 A1 Mar. 11, 2010

Related U.S. Application Data

(63) Continuation of application No. 11/780,627, filed on Jul. 20, 2007, now Pat. No. 7,601,356.

(60) Provisional application No. 60/832,553, filed on Jul. 21, 2006.

(51) Int. Cl.
*C12N 1/36* (2006.01)
*A61K 39/145* (2006.01)

(52) U.S. Cl. .................................... 435/440; 424/209.1

(58) Field of Classification Search ........................ None
See application file for complete search history.

(56) References Cited

U.S. PATENT DOCUMENTS

| | | | | |
|---|---|---|---|---|
| 3,992,522 | A | 11/1976 | Chanock et al. | |
| 4,071,618 | A | 1/1978 | Konobe et al. | |
| 4,634,666 | A | 1/1987 | Engleman et al. | |
| 4,659,569 | A | 4/1987 | Mitsuhashi et al. | |
| 5,166,057 | A | 11/1992 | Palese et al. | |
| 5,690,937 | A | 11/1997 | Parkin | |
| 5,716,821 | A | 2/1998 | Wertz et al. | |
| 5,789,229 | A | 8/1998 | Wertz et al. | |
| 5,820,871 | A | 10/1998 | Palese et al. | |
| 5,840,520 | A | 11/1998 | Clarke et al. | |
| 5,854,037 | A | 12/1998 | Palese et al. | |
| 5,922,326 | A | 7/1999 | Muiphy | |
| 6,001,634 | A * | 12/1999 | Palese et al. | 435/235.1 |
| 6,033,886 | A | 3/2000 | Conzelrnann | |
| 6,090,391 | A | 7/2000 | Parkin | |
| 6,146,642 | A | 11/2000 | Garcia-Sastre et al. | |
| 6,146,873 | A | 11/2000 | Kistner | |
| 6,168,943 | B1 | 1/2001 | Rose | |
| 7,037,707 | B2 * | 5/2006 | Webster et al. | 435/235.1 |
| 7,601,356 | B2 | 10/2009 | Jin et al. | |
| 2002/0164770 | A1 | 11/2002 | Hoffmann | |
| 2003/0035814 | A1 | 2/2003 | Kawaoka | |
| 2003/0147916 | A1 | 8/2003 | Ferko | |
| 2004/0029251 | A1 | 2/2004 | Hoffman | |
| 2004/0137013 | A1 | 7/2004 | Katinger | |
| 2005/0042229 | A1 | 2/2005 | Yang | |
| 2005/0054846 | A1 * | 3/2005 | Webster et al. | 536/23.72 |
| 2005/0158342 | A1 | 7/2005 | Kemble et al. | |
| 2005/0266026 | A1 | 12/2005 | Hoffmann et al. | |
| 2006/0019350 | A1 * | 1/2006 | Palese et al. | 435/69.1 |
| 2008/0175863 | A1 | 7/2008 | Jin et al. | |

FOREIGN PATENT DOCUMENTS

| | | |
|---|---|---|
| EP | 0702085 | 3/1996 |
| EP | 0864645 | 9/1998 |
| EP | 0780475 | 6/1999 |
| EP | 0863202 | 9/1999 |
| WO | WO 91/03552 | 3/1991 |
| WO | WO 93/21306 | 10/1993 |
| WO | WO 93/21306 A * | 10/1993 |
| WO | WO 96/10632 | 4/1996 |
| WO | WO 96/34625 | 11/1996 |
| WO | WO 97/06270 | 2/1997 |
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 00/53786 | 9/2000 |
| WO | WO 00/60050 | 10/2000 |
| WO | WO 02/24876 | 3/2002 |
| WO | WO 2008/133701 | 11/2008 |

OTHER PUBLICATIONS

Emmie de Wit. et al. Virus Research 2004, vol. 103, pp. 155-161.*
Bourmakina et al. J. Gene. Virol. 2003, vol. 84, pp. 517-527.*
NCBI Accession No. ABO21712 submitted by Fouchier et al. Mar. 2007.*
NCBI Accession No. AAA91325 published by May 2006 on line.*
Baez, Melvyn et al., 1980, "Gene Composition of High-Yielding Influenza Vaccine Strains Obtained by Recombination", The Journal of Infectious Diseases, 141 (3):362-365.
Banerjee and Barik, 1992, "Gene expression of vesicular stomatitis virus genome RNA", Virology. 188):417-428.
Barman Subrata et al., 2001, "Transport of viral proteins to the apical membranes and interaction of matrix protein with glycoproteins in the assembly of influenza viruses", Virus Research, 77:61-69.
Baron and Barrett, 1997, "Rescue of Rinderpest Virus from Cloned cDNA", J. Virol. 71:1265-1271.
Basler et al., 1999, "Mutation of Neuraminidase Cysteine Residues Yields Temperature-Sensitive Infuenza Viruses," J. of Virology 73(10):8095-8103.

(Continued)

*Primary Examiner* — Bao Li
(74) *Attorney, Agent, or Firm* — Grant Anderson LLP

(57) ABSTRACT

In certain aspects, the present invention provides methods for increasing the replication capacity of influenza viruses in hens' eggs and/or cell culture, recombinant and/or reassortant influenza viruses with increased replication capacity, and immunogenic and vaccine compositions comprising such recombinant and/or reassortant influenza viruses. In other aspects, the invention further provides nucleic acids encoding influenza genes associated with increased replication capacity, expression vectors comprising the nucleic acids of the invention, methods for making influenza viruses with increased replication capacity, and kits useful for practice of the methods.

2 Claims, 4 Drawing Sheets

OTHER PUBLICATIONS

Figure 1:
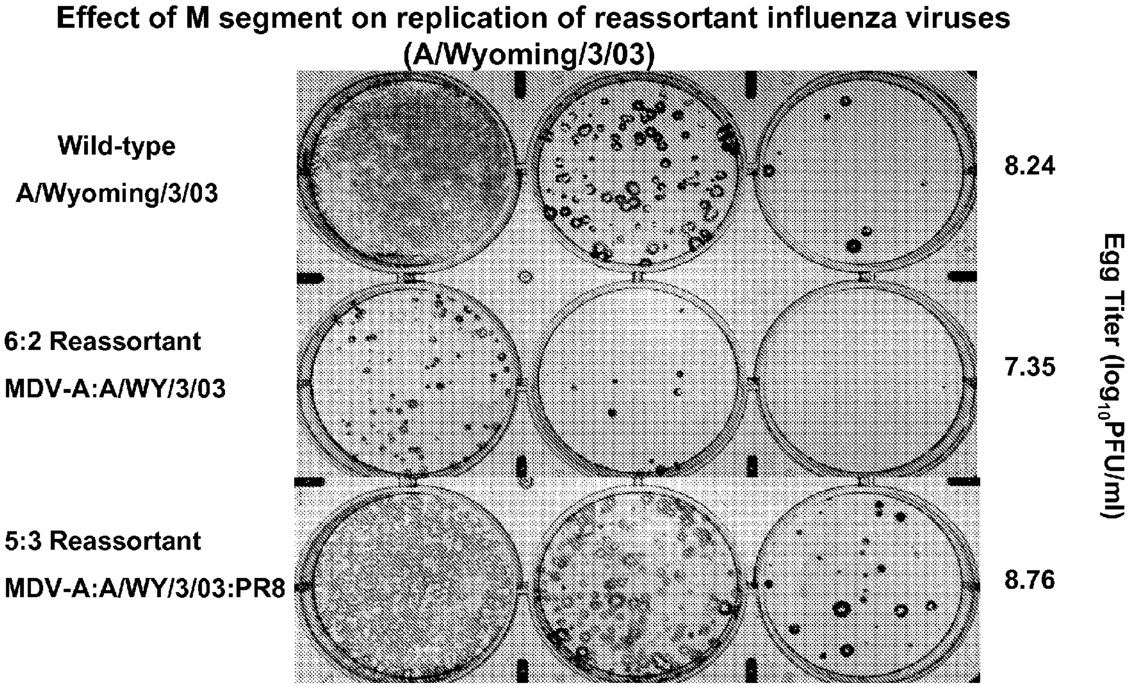

Beare et al., 1975, "Trials in Man with Live Recombinants Made from A/PRJ8/34 (HO N1) and Wild H3 N2 Influenza Viruses", Lancet 729-732.
Belshe et al. 1998 , "The efficacy of live attenuated, cold-adapted, trivalent, intranasal influenza virus vaccine in children ," N Eng\ J Med 338: 1405-12.
Belshe, 1995 "A Review of Attenuation of Influenza Viruses by Genetic manipulation", American Journal of Respiratory and Critical Care Medicine 152:S72-S75.
Bergmann, et al., 1995, "The relative amount of an influenza A virus segment present in the viral particle is not affected . . . ", J. of Gen. Virology, 76:3211-3215.
Bourmakina, Svetlana V. et al., 2003, "Reverse genetics studies on the filamentous morphology of influenza A virus" Journal of General Virology, 84:517-527.
Boyce et al., 2001, "Safety and immunogenicity of adjuvanted and unadjuvanted subunit influenza" k vaccines administered intranasally to healthy adults, Vaccine 19:217-226.
Boyer et al., 1994, "Infectious transcripts and eDNA clones of RNA viruses", Virology. 198:415-426.
Brandt et al., 2001, "Molecular Determinants of Virulence, Cell Tropism, and Pathogenic Phenotype of Infectious Bursal Disease Virus", Journal of Virology 75(24): 11974-11982.
Brigden and Elliott, 1996, "Rescue of a Segmented Negative-Strand RNA Virus Entirely from Cloned Complementary DNAS", Proc. Natl. Acad. Sci. USA 93:15400-15404.
Buchholz et al., 1999 "Generation of Bovine Resp. Syncytial Virus (BRSV) from cDNA: BRSV NS2 Is Not Essential for Virus Replication in Tissue Culture . . . " J. Virol. 73:251-259.
Bukreyev et al., 1996, "Recovery of infectious respiratory syncytial virus expressing an additional, foreign gene", J Virol. 70(10):6634-41.
Burleigh, Laura M. et al., 2005, "Influenza A Viruses with Mutations in the MI Helix Six Domain Display a Wide Variety of Morphological Phenotypes", Journal of Virology, 79(2):1262-1270.
Castrucci et al., 1995, "Reverse genetics system. for generation of an influenza A virus mutant containing a deletion of the carboxyl-terminal M2 .." J Virol. 69(5):2725-2728.
Chan, Winnie et al., 2008, "The cold adapted and temperature sensitive influenza A/Ann Arbor/6/60 virus, the master donor virus for live attenuated influenza vaccines; has multiple defects in replication at the restrictive temperature", Virology, doi:I0.I016/j.virol.2008.07.027.
Chen et al., 1999, "Influenza A virus NSI protein targets poly (A)-binding protein II of the cellular 3'-end processing machinery", EMBO 18: 2273-2283.
Chen, Benjamin J. et ai., 2005, "Influenza Virus Hemagglutinin (H3 Subtype) Requires Palmitoylation of Its Cytoplasmic Tail for Assembly: MI Proteins of Two Subtypes Differ in Their Ability to Support Assembly", Journal of Virology, 79(21):13673-13684.
Chen, Zhongying et al., 2006, "Genetic mapping of the cold-adapted phenotype of B/Ann Arbor./1/66, the master donor of virus for live attenuated influenza vaccines (FluMist®)", Virology, 345:416-423.
Chen, Zhongying et al., 2008, "Molecular studies of temperature-sensitive replication of the cold adapted B/Ann Arbor/1/66, the master donor virus for live attenuated influenza Flu Mist® vaccines", Virology, doi:10.1016/j.virol.2008.08.010.
Clarke et al., 2000, "Rescue of mumps virus from cDNA", J. Virol. 74(10):4831-38.
Collins et al., 1991, "Rescue of Synthetic Analogs of Respiratory Syncytial Virus Genomic RNA and Effect of Truncations and Mutations. on the Expresson . . . ", Proc. Nat. Acad. Sci. USA 88:9663-9667.
Collins et al., 1995, "Production of infectious human respiratory syncytial virus from cloned cDNA confirms an essential role . . . " PNAS 92: 11563-1567.
Collins et al., 1996, "Parainfluenza Viruses", Fields Virology, Lippincott-Raven Publishers, Phila., pp. 1205-1241.
Conzelmann et al., 1994, "Rescue ofsynthetie genomic RNA analogs of rabies virus by plasmid-encoded proteins", J Virol. 68(~):713-19.
Conzelmann et al., 1996, "Genetic engineering of animal RNA viruses", Trends Microbiol. 4(10):386-93.
Conzelmann et al., 1998, "Nonsegmented negative-strand RNA viruses: genetics and manipulation of viral genomes", Annu Rev Genet. 32:123-62.
Conzelmann, 1996, "Genetic manipulation of non-segmented negative-strand RNA viruses", J Gen Virol. 77 (Pt 3):381-89.
Cox, et al.; Identification of Sequence Changes in the Cold-Adapted, Live Attenuated Influenza..a Vaccine Strain A/Ann Arbor/6/60 (H2N2)/, Virology, 1988; 167: 554-567.
Cros, Jerome F. et al. 2003, "Trafficking of viral genomic RNA into and out of the nucleus: influenza, Thogoto and Borna disease viruses", Virus Research 95:3-12.
De and Banerjee, 1985, "Requirements and Functions of Vesicular Stomatitis Virus Land NS Proteins in the Transcription ..", Biochem. & Biophys. Res. Commun. 126:40-49.
De and Banerjee, 1993, "Rescue of synthetic analogs of genome RNA of human parainfluenza virus type 3", Virology, 96:344-348.
De and Banerjee, 1994, "Reverse genetics of negative strand RNA viruses," Indian J Biochem & Biophys. 31:367-376.
De la Luna et al., 1993, "Influenza virus naked RNA can be expressed upon transfection into cells coexpressing the three subunits . . . " J. Gen. Viroi. 74: 535-39.
De La Luna et al., 1995, "Influenza virus NS1 Protein Enhances the Rate of Translation Initiation of Viral rnRNAs", J. of Virol. 69: 2427-2433.
Dimock et al., 1993, "Rescue of synthetic analogs of genomic RNA and replicative-intermed. RNA of human parainfluenza virus type 3,", J Viroi. 67(5):2772-78.
Dreher and Hall, 1988, "Mutational Analysis or the Sequence and Structural Requirements in Brome Mosaic Virus RNA for Minus Strand Promoter Activity", J. Mol. Biol. 201:31-40.
Dreher et al., 1984, "Mutant Viral RNAs Synthesized in vitro Show Altered Aminoacylation and Replicase Template Activities", Nature 311: 171-175.
Dunn et al., 1995, "Transcription of a recombinant bunyavirus RNA template by transiently expressed bunyavirus proteins", Virology, 211: 133-43.
Durbin et al., 1997, "Recovery of infectious Human Parainfluenza Virus Type 3 from cDNA", Virol. 235:323-332.
Edwards et al., 1994, "A randomized controlled trial of cold adapted and inactivated vaccines for the prevention of influenza A disease", J Infeet Dis 169:68-76.
Egorov et al., 1998, "Transfectant Influenza A Viruses with Long Deletions in the NS1 Protein Grow Efficiently in Vero Cells", J. of Virology 72(8):6437-6441.
Elleman, C.I. et al., 2004, "The MI matrix protein controls the filamentous phenotype of influenza A virus", Virology, 321 :144-153.
Elliot et al., 1997, Abstract # 96 10.sup.th International conference on Negative Strand Viruses.
Elliott et al., 1991, "Some highlights of virus research in 1990", J Gen Virol. 72: 1761-79. Review.
Emerson and Yu, 1975, "Both NS and L Proteins are Required for in vitro RNA Synthesis by Vosicular Stomatitis Virus", J. Virol. 15:1348-1356.
Emmie de Wit. et al. Virus Research 2004, vol. 103, pp. 155-161.
Enami and Palese, 1991, "High-Efficiency Formation of Influenza Virus Transfectants", J. Viral. 65:2711-2713.
Enami et al., 1991, "An influenza virus containing nine different RNA segments", Virology. 185:291-198.
Enami et al., 1990, "Introduction of Site Specific Mutations into the Genome of Influenza Vints", Proc Natl Acad Sci USA 87: 3802-3805.
Enami et al., 2000, "Characterization of Influenza Virus NS I Protein by Using a Novel Helper-Virus Free Reverse Genetic System", J. of Virology 74(12):5556-5561.
Fahey and Schooley, 1992, "Status of Immune-Based Therapies in HN Infection and AIDS", Clin. Exp. Immunol. 88:1-5.
Flick, et al., "Promoter elements in the influenza vRNA terminal structure," RNA, 1996; 2(10):1046-1057.
Fodor et al., 1999, "Rescue of Influenza A Virus from Recombinant DNA", J. of Virology 73(11):9679-9682.
Fortes et al., 1994, "Influenza virus NS1 protein inhibits pre-rnRNA splicing and blocks mRNA nucleocytoplasmic transport", EMBO 1. 13: 704-712.

Furminger, "Vaccine Production", Textbook of Influenza, pp. 324-332; (1996).
Garcia-Sastre A, Palese P, 1993. "Genetic manipulation of negative-strand RNA virus genomes", Annu Rev Microbiol. 47:765-790.
Garcin et al., 1995, "A highly recombinogenic system for the recovery of infectious sendai paramyxovirus from cDNA: generation of a novel" EMBO J. 14: 6087-6094.
Ghendon, "Cold-Adagted, Live Influenza Vaccines Developed in Russia," Textbook of Influenza, Chapter 29, pp. 391-399; (1998).
Goto et al.,1997, "Mutations Affecting the Sensitivity of the Influenza Virus Neuraminidase to 4-Guanidino-2 4-Dideoxy-2 3 Dehydro-N-Acetyineuraminic Acid", Virol. 238:265-27.
Govorkova, E.A., et al., "African Green Monkey Kidney (Vero) Cells Provide an Alternative Host Cell ..",1. of Virology, Am. Soc. for Microbiology Aug. 1996 70(8):5519-5524.
Grosfeld et al., 1995, "RNA replication by respiratory syncytial virus (RSV) is directed by the N., P., and L proteins: transcription . . . " J. Viral. 69(9):5677-86.
Guan, Yi, et al., "Molecular Characterization of H9N2 Influenza Viruses: Were They the Donors of the "Internal" .. ?", Proc. Natl. Acad. Sci., U.S.A. Aug. 1999,96:9363-9367.
Hatada and Fukudo, 1992, "Binding of influenza A virus NS 1 protein to dsRNA in vitro", J. of Gen. Viral. 73: 3325-3329.
He et al., 1997, "Recovery of Infectious SV5 from Cloned DNA and Expression of a Foreign Gene", Virol. 237:249-260.
Herlocher et al., "Sequence Comparisons of *A/AA/6/60* Influenza Viruses: Mutations Which May Contribute to Attenuation" .. Virus Research, 42: 11-25; (1996).
Hoffman and Banerjee, 1997. :An Infectious Clone of Human Parainfluenza Virus Type 3, J. Virol. 71 :4272-4277.
Hoffman et al., "Ambisense" Approach for the Generation of Influenza A Virus: vRNA and mRNA Synthesis from One Template Virology, 267:310-317;_(2000).
Hoffman et al., "Eight-Plasmid Rescue System for Influenza A Virus", International Congress Series, 1219:1007-1013; (2001).
Hoffman et al., "Eight-Plasmid System for Rapid Generation of Influenza Virus Vaccines", Vaccine, 20:3165-3170; (2002).
Hoffman et al., 2002, "Rescue of influenza B virus from eight plasmids", PNAS 99: 11411-11416.
Hoffman et al., 2005, Multiple Gene Segments Control the Temperature Sensitivity and Attenuation Phenotypes of ca B/ Ann Arbor/I/66; Journal of Virology, 79( 17): 11014-11021.
Hoffmann et al., 2000, "A DNA transfection system for generation of influenza A virus from eight plasmids", PNAS 97(11):6108-6113.
Hoffmann et al. "Universal primer set for the full-length amplification of all influenza A viruses." Arch Virol. Dec. 2001; t 46(12):2275-89).
Hoffmann et al., 2000, "Unidirectional RNA polymerase I-polymerase II transcription system for the generation of influenza A virus . . . ", J. of Gen. Virology 81:2843-2847.
Hoffmann, Erich, Aufbau eines RNA-Polymerase I-Vektorsystems zur gezielten Mutagenese von Influenza A Viren, Gieben 1997 (Doctoral Dissertation).
Hoffmann; 1997, "Generation of an RNA-Polymerase Vector Syst. for the Select. Mutagenesis ..," Inaugural Dissertation of Sch. of Nat. Sciences, Justus Liebig U. Gieben.
Hoffmann et al., 2000 "Characterization of the Influenza A Virus Gene Pool in Avian Species in Southern China: Was H6N1 . . . ?" J. Virology 74(14):6309-6315.
Huang et al., 1990, "Determination of Influenza virus proteins required for genome replication", J Virol. 64(11):5669-73.
Hui, Eric Ka-Wai et al., 2003, "Basic Residues of the Helix Six Domain of Influenza Virus MI Involved in Nuclear Translocation of M1 Can Be Replaced by PTAP and YPDL Late Assembly Domain Motifs", Journal of Virology, 77(12):7078-7092.
Hui, Eric Ka-Wai et al., 2003, "Conserved cysteine and histidine residues in the putative zinc finger motif of the influenza A virus MI protein arc not critical for influenza virus replication", Journal of General Virology, 84:3105-3113.
Hui, Eric Ka-Wai et al., 2006, "Mutations in Influenza Virus M1 CCHH, the Putative Zinc Finger Motif, Cause Attenuation in Mice and Protect Mice against Lethal Influenza Virus Infection", Journal of Virology 80(12):5697-5707.
International Search Report and Written Opinion mailed: Sep. 22, 2008 for PCT/US07/73950 filed: Jul. 20, 2007 and published as: WO/2008/133701 on: Nov. 6, 2008.
Kaplan et al., 1985. "In vitro Synthesis of Infectious Poliovirus RNA", Proc. Natl. Acad. Sci. USA 82:8424-8428.
Katinger et al., "Attenuated Influenza Virus as a Vector for Mucosal Immunization against HIV-1",Vaccines, pp. 315-319, (1997).
Kato ct al., 1996, "Initiation of Sendai Virus Multiplication from Transfected cDNA or RNA with Negative or Positive Sense", Genes to Cells I :569-579.
Keitel, et al., "Live Cold-Adapted, Reassortant Influenza Vaccines (USA)," Textbook of Influenza, Chapter 28, pp. 373-390. (1998).
Kimura et al., 1993, "An in vivo study of the replication origin in the influenza virus complementary RNA", J Biochem (Tokyo) 113:88-92.
Kimura et al., 1992, "Transcription of a recombinant influenza virus RNA in cells that can express the influenza virus RNA polymerase . . . ", J Gen Virol. 73: 1321-28.
Klimov et al., 1991, "Correlation of amino acid residues in the M1 and M2 proteins of influenza virus with high yielding properties" Virus Res. 19:105-114.
Kobayashi et at, 1992, Reconstitution of influenza virus RNA polymerase from three subunits expressed using recombinant baculovirus system. Virus Res. 22:235-245.
Konarska et al., 1990, "Structure ofRNAs replicated by the DNA-dependent T7 RNA polymerase", Cell. 63(3):609-18.
Krystal et al., 1986, "Expression of the Three Influenza Virus Polymerase Proteins in a Single Cell Allows Growth . . . ", Proc. Natl. Acad. Sci. USA 83:2709-2713.
Kunkel, 1985, "Rapid and Efficient Site-Specific Mutagenesis without Phenotypic Selection", Proe. Natl. Acad. Sci. USA 82:468-492.
Lamb et al., 1996, Fundamental Virology 3.sup.rd ed. Chapters 20 and 21.
Lawson et al., 1995, "Recombinant vesicular stomatitis viruses from DNA", Proc Natl Acad Sci USA.92:4477-4481.
Levis et al., 1986, "Deletion Mapping of Sindbis Virus DI RNAs Derived from cDNAs Defines the Sequences Essential for Replication and Packaging", Cell 44: 137-145.
Li et al., 1999, "Recombinant influenza A virus vaccines for the pathogenic human N/Hong Kong/97 (H5NI) viruses," J. of Infectious Diseases, 179: 1132-8.
Liu, Teresa et al., 2002, "Association of Influenza Virus Matrix Protein with Ribonucleoproteins May Control Viral Growth and Morphology", Virology, 304:89-96.
Liu, Teresa et al., 2002, "Restriction of Viral Replication by Mutation of the Influenza Virus Matrix Protein", Journal of Virology, 76(24):13055-13061.
Liu, Teresa et al., 2004, "Introduction of a Temperature-Sensitive Phenotype into Influenza A/WSN/33 Virus by Altering the Basic Amino Acid Domain of Influenza Virus Matrix Protein", Journal of Virology, 78(18):9585-9591.
Liu, Teresa et al., 2005, "Attenuating Mutations of the Matrix Gene of Influenza A/WSN/33 Virus", Journal of Virology, 79(3):1918-1923.
Lu, et al., 2005, "Improvement of Influenza A/Fujian/411/02 (H3N2) Virus Growth in Embryonated Chicken Eggs by Balancing the Hemagglutinin and Neuraminidase Activities, Using Reverse Genetics", The Journal of Virology, 79(11):6763-6771.
Luyues et al., 1989, "Amplification, Expression, and Packaging of a Foreign Gene by Influenza Virus", Ce1159: 1107-1113.
Maassab et al., "Evaluation of a Cold-Recombinant Influenza Virus Vaccine in Ferrets", J. of Infectious Diseases, 146:780-790; (1982).
Maassab, "Adaptation and growth characteristics of influenza virus at 25 degrees C", Nature, 213:612-614 (1967).
McCullers, Jonathan A. et al., (2005) "A single amino acid change in the C-tenninal domain of the matrix protein MI of influenza B virus confers mouse adaptation and virulence", Virology, 336:318-326.
Mena et al., 1994, "Synthesis of biologically active influenza virus core proteins using a vaccinia virus-17 RNA polymerase expression system", J Gen Virol. 75:2109-14.
Mena et al., 1996, "Rescue of a Synthetic Chloramphcnicol Acetyltransferase RNA into Influenza Virus-Like Particles Obtained ft. Recombinant Plasmids" J. Virol. 70: 5016-5024.

Merten et al., "Production of influenza virus in Cell Cultures for Vaccine Preparation", Novel Strategies in Design and Production of Vaccines, pp. 141-151; (1996).
Moyer et al., 1991, "Assembly and transcription of synthetic vesicular stomatitis virus nucleocapsids", J Virol. 65(5):2170-88.
Murphy & Coelingh, "Principles Underlying the Development and Use of Live Attenuated Cold-Adapted Influenza A and B Virus Vaccines", Viral Immunol 15:295-323' (2002).
Muster et al., 1991, "An influenza A virus containing influenza B virus 5' and 3' noncoding regions on the neuraminidase gene .. :", Proc Natl Acad Sci USA 88:5177-81.
Naito and Isbihama, 1976, "Function and Structure of RNA Polymerase from Vesicular Stomatitis Virus", J. Biol. Chern. 251:4307-4314.
Nara et al., 1987, "Simple, Rapid, Quantitative, Syncytium-Forming Micorassay for the Detection of Human Immunodeficiency . . . " AIDS Res. Hum. Retroviruses 3:283-302.
NCBI Accession No. AB021712 submitted by Fouchier et al. Mar. 2007.
NCBI Accession No. CAA30882 finally submitted by Lam RA in1989.
Nemeroff ct al., 1998, "Influenza Virus NS1 Protein Interacts with the Cellular 30 kDa Subunit of CPSF and Inhibits 3' End Fonnation .." Mol. Celll :991-1000.
Neumann et al., 1994, "RNA Polynlerase I-Mediated Expression of Influenza Viral RNA Molecules", Virol. 202:477-479.
Neumann et al.. 1999, "Generation of influenza A viruses entirely from cloned cDNAs", PNAS 96(16):9345-9350.
Neumann, et al., "Genetic Engineering of Influenza and Other Negative-Strand RNA Viruses Containing Segmented Genomes," Advances in Virus Research, 1999; 53: 265-300.
Nichol et al. 1999, "Effectiveness oflive, attenuated intranasal influcnza virus vaccine in healthy, working adults: a randomized controlled trial", JAMA 282:137-44.
Palese et al., 1996, "Negative-Strand RNA Viruses: Genetic Engineering and Applications", Proc. Natl. Acad. Sci. USA 93,11354-11358.
Park et al., 1991, "Rescue of a Foreign Gene by Sendai Virus", Proc. Natl. Acad. Sci. USA 88:5537-5541.
Parkin et al., "Temperature Sensitive Mutants of Influenza A Virus Generated by Reverse Genetics . . . ,", Virus Res., 46:31-44; (1996).
Parkin N. et al., "Genetically Engineered Live Attenuated Influenza A Virus Vaccine Candidates", J. Virol, pp. 2772•2778; (1997).
Pattnaik et al., 1991, "Cells that express all five proteins of vesicular stomatitis virus from cloned cDNAs support replication .." Proc Natl Acad Sci USA 88:1379-83.
Peeters et al., 1999, "Rescue of Newcastle Disease Virus from Cloned cDNA: Evidence thal Cleavability of the Fusion Protein . . . ", J. Virol. 73:5001-5009.
Pekosz et al., 1999, "Reverse genetics of negative-strand RNA viruses: closing the circle", Proc Natl Acad Sci USA. 96(16):8804-16.
Percy et al., 1994, "Expression of a foreign protein by influenza A virus", J Virol 68(7):4486-92.
Perez, Daniel R. et al., 1998 "The Matrix 1 Protein of Influenza A Virus Inhibits The Transciptase Activity of a Model", Article No. VY989318 Virology, 249:52-61.
Pleschka et al., 1996, "A Plasmid-Based Reverse Genetics System for Influenza A Virus", J. Virol. 70:4188-4192.
Qiu et. al., 1994, "The influenza virus NS1 protein is a poly(A)-binding protein that inhibits nuclear export of rnRNAs containing poly(A)", J Virol. 68(4):2425-32.
Qui et.al., 1995. "The influenza virus NS 1 protein binds to a specific region in human U6 snRNA and inhibits U6-U2 and U6-U4 snRNA ..", RNA Society 1:304-16.
Racaniello et al., 1981. "Cloned Poliovirus Complementary DNA is Infectious in Mammalian Cells", Science 214:916-919.
Radecke et al., "Reverse Genetics Meets the Nonsegmented Negative-Strand RNA Viruses", Medical Virology, vol. 7: 49-63 (1997).
Radecke et al., 1995, "Rescue of measles viruses from cloned DNA", EMBO J. 14(23):5773-84.
Roberts and Rose, 1998, "Recovery of Negative-Strand RNA Viruses from Plasmid DNAs: a Positive Approach Revitalizes a Negative Field", Virol. 247: 1-6.
Roberts, Paul C., et al., 1998, "The MI and M2 Proteins of Influenza A Virus Are Important Determinants in Filamentous Particle Formation" Virology 240: 127-137.
Rose 1996, "Positive Strands to the Rescue Again: A Segmented Negative-Strand RNA Virus Derived from Cloned . . . "~PNAS USA 94: 14998-15000.
Schickli et al., 2001, "Plasmid-only rescue of influenza A virus vaccine candidates", Philos Trans Society of London Ser B 356:1965-1973.
Schlesinger, 1995. "RNA viruses as vectors for the expression of heterologous proteins", Mol Biotechnol. 3:155-65.
Schnell et al., 1994, "Infectious Rabies Viruses from Cloned cDNA", EMBO J. 13:4195-4203.
Scholtissek, et al., "The Nucleoprotein as a Possible Major Factor in Determining Host Specificity of Influenza H3N2 Viruses," Virology, 1985; 147:287-294.
Seong et al., 1992, "A new method for reconstituting intluenza polymerase and RNA in vitro: a study of the promoter elements for cRNA ..", Virology 186:247-60.
Sidhu et al., 1995, "Rescue of synthetic measles virus minireplicons: measles genomic termini direct efficient expression . . . " Virology. 208(2):800-07.
Smeenk, Cecilia A. et al., 1994, "The Influenza Virus Variant NFM. I1I47-MA Possesses Single Amino Acid Replacements in the Hemagglutinin, Controlling Virulence, and in the Matrix Protein, Controlling \Virulence as well as Growth", Journal of Virology, 68(1):530-534.
Snyder et al., "Four Viral Genes Independently Contribute to Attenuation of Live Influenza *Al* Ann Arbor/6/60 (H2N2) Cold-Adapted . . . ", J. Viro1., 62:488-95; (1988).
Subbarao et al., "The Attenuation Phenotype Conferred by the M Gene of the Influenza *A/Ann* Arbor/6/60 Cold-Adapted Virus (H2N2) on the . . . " Virus Res. 25:37-50; (1992).
Subbarao et al., 1995, "Sequential addition of temperature-sensitive missense mutations into the PB2 gene of influenza A . . . " J. of Virology 69(10):5969-5977.
Szewczyk et al., 1988, "Purification, Thioredoxin Renaturation, and Reconstituted Activity of the Three Subunits of the Intluenza ..", Proc. Natl. Acad. Sci. USA 85:7907-7911.
Taylor et al., 1990, "Newcastle Disease Virus Fusion Protein Expressed in a Fowlpox Virus Recombinant Confers Protection in Chickens", J. Virol. 64:1441-1450.
Ward et al., 1988, "Direct Measurement of the Poliovirus R.'NA Polymerase Error Frequency in Vitro", J. Virol. 62:558-562.
Webby et al., 2004, "Responsiveness to a pandemic alert: use of reverse genetics for rapid development of influenza vaccines", Lancet 363:1099-1103.
Whelan et al., 1995, "Efficient recovery of infectious vesicular stomatitis virus entirely from cDNA clones", Proc.Natl.Acad.Sci. USA 92:8388-8392.
Xu, Xiyan, et al., 1999"Genetic Characterization of the Pathogenic Influenza A /Goose/Guangdong/I/96 (HSN1) Virus: . . . ", Article ill viro. 1999.9820. Virology 261 :15-19.
Yamanaka et al., 1991, "In vivo analysis of the promoter structure of the influenza virus RNA genome using a transfection system . . . ," Proc Natl Acad Sci USA 88: 5369-5373.
Yasuda, J. et al., 1993, "Regulatory effects of matrix protein variations on influenza virus growth", Archives ofVirology, 133:283-294.
Yasuda, Jiro et al., 1994, "Growth Control of Influenza A Virus by MI Protein: Analysis of Transfectant Viruses Carrying the Chimeric M Gene", Journal of Virology, 68(12):8141-8146.
Yu et al., 1995, "Functional cDNA clones of the human respiratory syncytial (RS) virus N, P, and L proteins support replication . . . ", J Virol. 69(4) 2412-2419.
Yusoff et al., 1987, "Nucleotide Sequence Analysis of the L Gene of Newcastle Disease Virus: Homologies with Sendi and Vesicular Stomatitis.", Nucleic Acids Res. 15:3961-76.
Zaghouani et al., 1991, "Induction of antibodies to the envelope protein of the human immunodeficiency virus by immunization ..", Proc. Natl. Acad Sci. USA 88:5645-5649.

Zaghouani et al., 1992, "Cells Expressing an H Chain to Gene Carrying Viral T Cell Epitope Are Lysed by Specific Cytolytic T Cells" J. Immunol. 148:3604-3609.
Zhang and Air, 1994, "Expression of Functional Influenza Virus A Polymerase Proteins and Template from Cloned cDNAs ..", Biochem. & Biophys. Res. Commun. 200:95-101.
Zhang et al., "Persistence of four related human immunodeficiency virus subtypes during the course of zidovudine therapy . . . ", J. Virol. 199468: 425-432.
Zhou, Yan, et al., "Membrane-Anchored Incorporation of a Foreign Protein in Recombinant Influenza Virions", Article No. VY989169, Virology, 1998, vol. 246 pp. 83-94.
Zobel et al., 1993, "RNA polymerase I catalyzed transcription of insert viral cDNA", Nucleic Acids Res. 21(16):3607-14.
International Preliminary Report on Patentability mailed: Jan. 27, 2009 for PCT/US07/73950 filed: Jul. 20, 2007 and published as: WO/2008/133701 on: Nov. 6, 2008.
Ito et al., "Evolutionary Analysis of the Influenza A Virus M Gene with Comparison of the M1 and M2 Proteins" Journal of Virology, vol. 65, No. 10, Jan. 1, 1991, pp. 5491-5498.
Office Action mailed on: Jun. 2, 2009 in U.S. Appl. No. 11/780,627, filed Jul. 20, 2007, Published as: US2008/0175863 on Jul. 24, 2008 and issued as: 7,601,356 on Oct. 13, 2009.
Office Action mailed on: Dec. 12, 2008 in U.S. Appl. No. 11/780,627, filed Jul. 20, 2007, Published as: US2008/0175863 on Jul. 24, 2008 and issued as: 7,601,356 on Oct. 13, 2009.

* cited by examiner

Effect of M segment on replication of reassortant influenza viruses (A/Wyoming/3/03)

Wild-type
A/Wyoming/3/03 — 8.24

6:2 Reassortant
MDV-A:A/WY/3/03 — 7.35

5:3 Reassortant
MDV-A:A/WY/3/03:PR8 — 8.76

Egg Titer ($\log_{10}$ PFU/ml)

Sequence comparisons of several influenza viruses

```
                  (1)  1         10        20        30        40        54
MDV-A M1     (1)  MSLLTEVETYVLSIIPSGPLKAEIAQRLEDVFAGKNTDLEALMEWLKTRPILSP
pr8-M        (1)  MSLLTEVETYVLSIIPSGPLKAEIAQRLEDVFAGKNTDLEVLMEWLKTRPILSP
Sendai-M1    (1)  MSLLTEVETYVLSIVPSGPLKAEIAQRLEDVFAGKNTDLEALMEWLKTRPILSP
SY97_M1      (1)  MSLLTEVETYVLSIVPSGPLKAEIAQRLEDVFAGKNTDLEALMEWLKTRPILSP
WY03-M1      (1)  MSLLTEVETYVLSIVPSGPLKAEIAQRLEDVFAGKNTDLEALMEWLKTRPILSP

                  (55) 55   60        70        80        90        108
MDV-A M1    (55)  LTKGILGFVFTLTVPSERGLQRRRFVQNALNGNGDPNNMDRAVKYRKLKREIT
pr8-M       (55)  LTKGILGFVFTLTVPSERGLQRRRFVQNALNGNGDPNNMDKAVKYRKLKREIT
Sendai-M1   (55)  LTKGILGFVFTLTVPSERGLQRRRFVQNALNGNGDPNNMDKAVKLYRKLKREIT
SY97_M1     (55)  LTKGILGFVFTLTVPSERGLQRRRFVQNALNGNGDPNNMDKAVKLYRKLKREIT
WY03-M1     (55)  LTKGILGFVFTLTVPSERGLQRRRFVQNALNGNGDPNNMDKAVKLYRKLKREIT

                  (109) 109    120       130       140       150       162
MDV-A M1   (109)  FHGAKEIALSYSAGALASCMGLIYNRMGAVTTEVVLGLVCEQIADSQHRSH
pr8-M      (109)  FHGAKEISLSYSAGALASCMGLIYNRMGAVTTEVAFGLVCEQIADSQHRSH
Sendai-M1  (109)  FHGAKEIALSYSAGALASCMGLIYNRMGAVTTEVAFGLVCATCEQIADSQHRSH
SY97_M1    (109)  FHGAKEIALSYSAGALASCMGLIYNRMGAVTTEVAFGLVCATCEQIADSQHRSH
WY03-M1    (109)  FHGAKEIALSYSAGALASCMGLIYNRMGAVTTEVAFGLVCATCEQIADSQHRSH

                  (163) 163  170       180       190       200       216
MDV-A M1   (163)  RQMVTTTNPLIRHENRMVLASTTAKAMEQMAGSSEQAAEAMEVASQARQMVQAM
pr8-M      (163)  RQMVTTTNPLIRHENRMVLASTTAKAMEQMAGSSEQAAEAMEVASQARQMVQAM
Sendai-M1  (163)  RQMVATTNPLIRHENRMVLASTTAKAMEQMAGSSEQAAEAMEIASQARQMVQAM
SY97_M1    (163)  RQMVATTNPLIRHENRMVLASTTAKAMEQMAGSSEQAAEAMEIASQARQMVQAM
WY03-M1    (163)  RQMVATTNPLIRHENRMVLASTTAKAMEQMAGSSEQAAEAMEIASQARQMVQAM

                  (217) 217       230       240       252
MDV-A M1   (217)  RVIGTHPSSSAGLKNDLLENLQAYQKRMGVQMQRFK
pr8-M      (217)  RTIGTHPSSSAGLKNDLLENLQAYQKRMGVQMQRFK
Sendai-M1  (217)  RAIGTHPSSSTGLRDDLLENLQTYQKRMGVQMQRFK
SY97_M1    (217)  RAVGTHPSSSTGLRDDLLENLQTYQKRMGVQMQRFK
WY03-M1    (217)  RAIGTHPSSSTGLRDDLLENLQTYQKRMGVQMQRFK
```

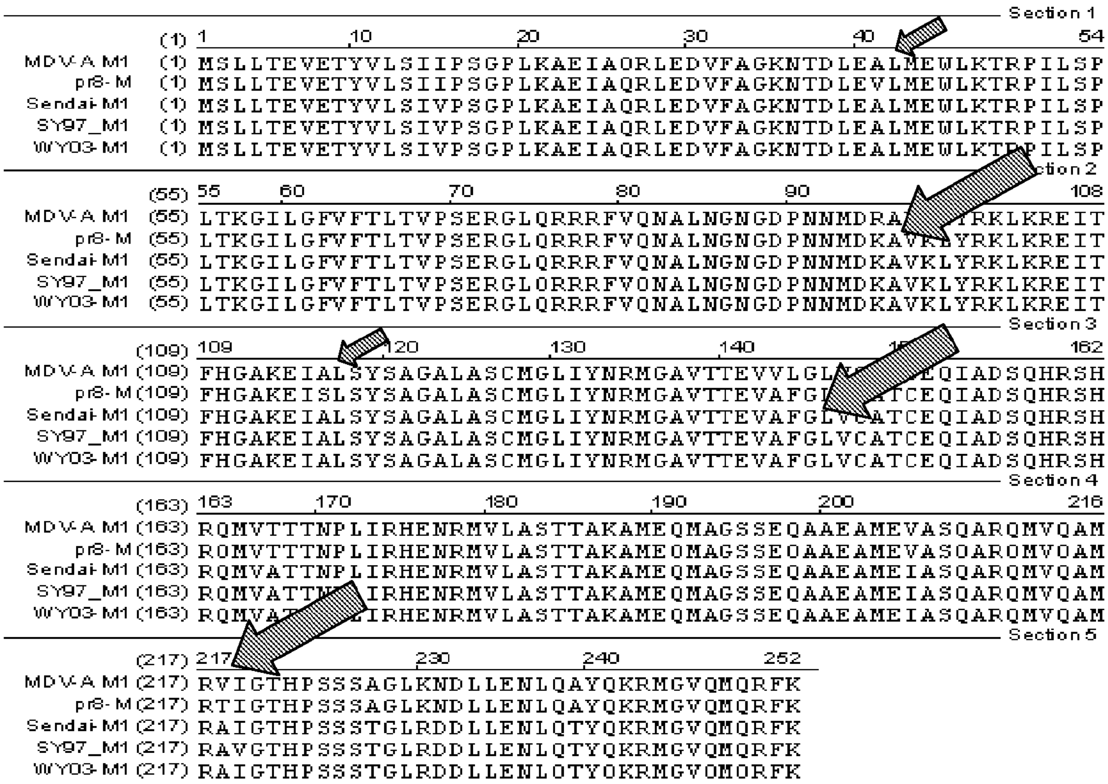

Fig 2.

Effect of the PR8 M1 residue on 6:2 ressortant replication in eggs

| | Average Titer (log10PFU/ml) | Stdev |
|---|---|---|
| Control Group | | |
| 6:2 MDV-M | 7.53 | 0.14 |
| wt Wyoming | 8.36 | 0.34 |
| 5:3 WYO-M | 8.56 | 0.11 |
| 5:3 PR8-M | 8.68 | 0.10 |
| Group #1: Changing MDV -> PR8 Sites | | |
| 41 | 6.45 | 0.51 |
| 95 | 7.67 | 0.14 |
| 116 | 7.51 | 0.43 |
| 218 | 7.73 | 0.17 |
| 143-144 | 7.37 | 0.55 |
| 95-143-144 | 7.31 | 0.66 |
| 95-218 | 5.89 | 0.47 |
| 143-144-218 | 7.75 | 0.09 |
| 95-143-144-218 | 8.46 | 0.13 |

Fig 3.

Effect of MDV-A M1 residues on replication of 5:3 reassortant (M-PR8) in Eggs

| AA position With MDV-A residue | Virus titer (log10PFU/ml) | Stdev |
|---|---|---|
| 95 | 7.11 | 0.02 |
| 143 | 7.19 | 0.85 |
| 144 | 6.96 | 0.18 |
| 143-144 | 6.63 | 0.05 |
| 218 | 7.84 | 0.31 |
| 95-143-144 | 7.52 | 0.14 |
| 143-144-218 | 6.67 | 0.25 |
| 95-143-144-218 | 6.78 | 0.88 |

Fig 4.

SEQUENCE LISTING

```
<160> NUMBER OF SEQ ID NOS: 5

<210> SEQ ID NO 1
<211> LENGTH: 252
<212> TYPE: PRT
<213> ORGANISM: Influenza A virus

<400> SEQUENCE: 1

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60
```

-continued

Thr Leu Thr Val Pro Ser Glu Arg Gly Leu Gln Arg Arg Arg Phe Val
65 70 75 80

Gln Asn Ala Leu Asn Gly Asn Gly Asp Pro Asn Asn Met Asp Arg Ala
85 90 95

Val Lys Leu Tyr Arg Lys Leu Lys Arg Glu Ile Thr Phe His Gly Ala
100 105 110

Lys Glu Ile Ala Leu Ser Tyr Ser Ala Gly Ala Leu Ala Ser Cys Met
115 120 125

Gly Leu Ile Tyr Asn Arg Met Gly Ala Val Thr Thr Glu Val Val Leu
130 135 140

Gly Leu Val Cys Ala Thr Cys Glu Gln Ile Ala Asp Ser Gln His Arg
145 150 155 160

Ser His Arg Gln Met Val Thr Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Val Ala Ser Gln
195 200 205

Ala Arg Gln Met Val Gln Ala Met Arg Val Ile Gly Thr His Pro Ser
210 215 220

Ser Ser Ala Gly Leu Lys Asn Asp Leu Leu Glu Asn Leu Gln Ala Tyr
225 230 235 240

Gln Lys Arg Met Gly Val Gln Met Gln Arg Phe Lys
245 250

<210> SEQ ID NO 2
<211> LENGTH: 252
<212> TYPE: PRT
<213> ORGANISM: Influenza A virus

<400> SEQUENCE: 2

Met Ser Leu Leu Thr Glu Val Glu Thr Tyr Val Leu Ser Ile Ile Pro
1 5 10 15

Ser Gly Pro Leu Lys Ala Glu Ile Ala Gln Arg Leu Glu Asp Val Phe
20 25 30

Ala Gly Lys Asn Thr Asp Leu Glu Val Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Val
65 70 75 80

Gln Asn Ala Leu Asn Gly Asn Gly Asp Pro Asn Asn Met Asp Lys Ala
85 90 95

Val Lys Leu Tyr Arg Lys Leu Lys Arg Glu Ile Thr Phe His Gly Ala
100 105 110

Lys Glu Ile Ser Leu Ser Tyr Ser Ala Gly Ala Leu Ala Ser Cys Met
115 120 125

Gly Leu Ile Tyr Asn Arg Met Gly Ala Val Thr Thr Glu Val Ala Phe
130 135 140

Gly Leu Val Cys Ala Thr Cys Glu Gln Ile Ala Asp Ser Gln His Arg
145 150 155 160

Ser His Arg Gln Met Val Thr Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Val Ala Ser Gln
195 200 205

Ala Arg Gln Met Val Gln Ala Met Arg Thr Ile Gly Thr His Pro Ser
210 215 220

Ser Ser Ala Gly Leu Lys Asn Asp Leu Leu Glu Asn Leu Gln Ala Tyr
225 230 235 240

Gln Lys Arg Met Gly Val Gln Met Gln Arg Phe Lys
245 250

<210> SEQ ID NO 3
<211> LENGTH: 252
<212> TYPE: PRT
<213> ORGANISM: Influenza A virus

<400> SEQUENCE: 3

Met Ser Leu Leu Thr Glu Val Glu Thr Tyr Val Leu Ser Ile Val Pro
1 5 10 15

Ser Gly Pro Leu Lys Ala Glu Ile Ala Gln Arg Leu Glu Asp Val Phe
20 25 30

Ala Gly Lys Asn Thr Asp Leu Glu Ala Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Val
65 70 75 80

Gln Asn Ala Leu Asn Gly Asn Gly Asp Pro Asn Asn Met Asp Lys Ala
85 90 95

Val Lys Leu Tyr Arg Lys Leu Lys Arg Glu Ile Thr Phe His Gly Ala
100 105 110

Lys Glu Ile Ala Leu Ser Tyr Ser Ala Gly Ala Leu Ala Ser Cys Met
115 120 125

Gly Leu Ile Tyr Asn Arg Met Gly Ala Val Thr Thr Glu Val Ala Phe
130 135 140

Gly Leu Val Cys Ala Thr Cys Glu Gln Ile Ala Asp Ser Gln His Arg
145 150 155 160

Ser His Arg Gln Met Val Ala Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Ile Ala Ser Gln
195 200 205

Ala Arg Gln Met Val Gln Ala Met Arg Ala Ile Gly Thr His Pro Ser
210 215 220

Ser Ser Thr Gly Leu Arg Asp Asp Leu Leu Glu Asn Leu Gln Thr Tyr
225 230 235 240

Gln Lys Arg Met Gly Val Gln Met Gln Arg Phe Lys
245 250

<210> SEQ ID NO 4
<211> LENGTH: 252
<212> TYPE: PRT
<213> ORGANISM: Influenza A virus

<400> SEQUENCE: 4

Met Ser Leu Leu Thr Glu Val Glu Thr Tyr Val Leu Ser Ile Val Pro
1 5 10 15

Ser Gly Pro Leu Lys Ala Glu Ile Ala Gln Arg Leu Glu Asp Val Phe

```
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Ala Val Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250


<210> SEQ ID NO 5
<211> LENGTH: 252
<212> TYPE: PRT
<213> ORGANISM: Influenza A virus

<400> SEQUENCE: 5

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
```

-continued

```
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Ala Ile Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250
```

METHODS AND COMPOSITIONS FOR INCREASING REPLICATION CAPACITY OF AN INFLUENZA VIRUS

1. CROSS REFERENCE TO RELATED APPLICATIONS

This application claims the benefit under 35 U.S.C. §119 (e) of U.S. Provisional Application No. 60/832,553 filed Jul. 21, 2006, the disclosure of which is incorporated herein in its entirety for all purposes.

2. FIELD OF THE INVENTION

In certain aspects, the present invention provides methods for increasing the replication capacity of influenza viruses in hens' eggs and/or cell culture, recombinant and/or reassortant influenza viruses with increased replication capacity, and immunogenic and vaccine compositions comprising such recombinant and/or reassortant influenza viruses. In other aspects, the invention further provides nucleic acids encoding influenza genes associated with increased replication capacity, expression vectors comprising the nucleic acids of the invention, methods for making influenza viruses with increased replication capacity, and kits useful for practice of the methods.

3. BACKGROUND

Influenza viruses are made up of an internal ribonucleoprotein core containing a segmented single-stranded RNA genome and an outer lipoprotein envelope lined by a matrix protein. Influenza A and B viruses each contain eight segments of single stranded RNA with negative polarity. The influenza A genome encodes at least eleven polypeptides. Segments 1-3 encode the three polypeptides, making up the viral RNA-dependent RNA polymerase. Segment 1 encodes the polymerase complex protein PB2. The remaining polymerase proteins PB1 and PA are encoded by segment 2 and segment 3, respectively. In addition, segment 1 of some influenza A strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2 (NEP), two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and BM2. The smallest segment encodes two products: NS1 is translated from the full length RNA, while NS2 is translated from a spliced mRNA variant.

Vaccines capable of producing a protective immune response specific for influenza viruses have been produced for over 50 years. Vaccines can be characterized as whole virus vaccines, split virus vaccines, surface antigen vaccines and live attenuated virus vaccines. While appropriate formulations of any of these vaccine types is able to produce a systemic immune response, live attenuated virus vaccines are also able to stimulate local mucosal immunity in the respiratory tract.

To date, all commercially available influenza vaccines in the United States have been propagated in embryonated hens' eggs. Although influenza virus generally grows well in hens' eggs, some influenza vaccine strains, such as the prototype A/Fujian/411/02 strain that circulated during the 2003-04 season, do not replicate well in embryonated hens' eggs, and have to be isolated by cell culture in a costly and time consuming procedure.

The ability of certain influenza virus strains to replicate to high titer in embryonated hens' eggs has been mapped to the M1 and M2 genes. See Klimov et al., 1991, *Virus Res.* 19:105-114. However, these studies identified only a single residue in the M1 gene that correlates with increased viral titer. Accordingly, identification of additional M1 residues associated with increased viral titer is needed to permit design and construction of recombinant and/or reassortant influenza viruses with increased replication capacity. These and other unmet needs are provided by the present invention.

4. SUMMARY

The present invention relates to methods and compositions for increasing the replication capacity of influenza viruses in, for example, embryonated hens' eggs and/or cell culture. The invention is based, in part, on the identification of particular M1 protein amino acids associated with increased replication capacity. By using an M gene encoding an M1 protein that comprises one or more of these particular amino acids, improved influenza viral yields can be achieved.

Accordingly, in a first aspect, the invention provides a method for increasing the replication capacity of an influenza virus that comprises altering an amino acid at a position corresponding to at least one of position 95, 143, 144, or 218 of the M1 protein of influenza strain MDV-A, thereby increasing the replication capacity of the influenza virus. It is specifically contemplated that conservative and non-conservative amino acid substitutions at these positions are within the scope of the invention. In certain embodiments, the amino acid corresponding to position 218 is not altered to be a threonine (T).

The amino acid(s) of the M1 protein can be altered by any method known to one skilled in the art, without limitation. In one embodiment, the M1 protein is altered by changing the nucleotide sequence of a gene encoding the M1 protein.

In certain embodiments, the amino acid at the position corresponding to position 95 is altered. In certain embodiments, the amino acid at the position corresponding to position 95 is altered to be lysine (K). In certain embodiments, the amino acid at the position corresponding to position 143 is altered. In certain embodiments, the amino acid at the position corresponding to position 143 is altered to be alanine (A). In certain embodiments, the amino acid at the position corresponding to position 144 is altered. In certain embodiments, the amino acid at the position corresponding to position 144 is altered to be phenylalanine (F). In certain embodiments, the amino acid at the position corresponding to position 218 is altered. In certain embodiments, the amino acid at the position corresponding to position 218 is altered to be isoleucine (I).

In certain embodiments, the method for increasing the replication capacity of an influenza virus comprises altering amino acids at least two positions corresponding to position 95, 143, 144, or 218 of the M1 protein of influenza strain MDV-A, thereby increasing the replication capacity of the influenza virus. In certain embodiments, the method for increasing the replication capacity of an influenza virus comprises altering amino acids at least three positions corresponding to position 95, 143, 144, or 218 of the M1 protein of influenza strain MDV-A, thereby increasing the replication capacity of the influenza virus. In certain embodiments, the method for increasing the replication capacity of an influenza virus comprises altering amino acids at positions corresponding to positions 95, 143, 144, and 218 of the M1 protein of influenza strain MDV-A, thereby increasing the replication capacity of the influenza virus. In certain embodiments, an amino acid at a position corresponding to at least one of position 95, 143, or 144 is altered. In certain embodiments, an amino acid at a position corresponding to at least one of position 95, 143, or 144 is altered and an amino acid at a position corresponding to position 218 is altered. In certain embodiments, the amino acid at the position corresponding to position 95 is altered to be lysine (K), the amino acid at the position corresponding to position 143 is altered to be alanine (A), the amino acid at the position corresponding to position 144 is altered to be phenylalanine (F), and the amino acid at the position corresponding to position 218 is altered to be isoleucine (I).

In certain embodiments, the replication capacity of the influenza virus is increased at least 2-fold relative to the same influenza virus in the absence of the alteration. In certain embodiments, the replication capacity of the influenza virus is increased at least 4-fold relative to the same influenza virus in the absence of the alteration. In certain embodiments, the replication capacity of the influenza virus is increased at least 8-fold relative to the same influenza virus in the absence of the alteration. In certain embodiments, the replication capacity of the influenza virus is increased at least 10-fold relative to the same influenza virus in the absence of the alteration.

In certain embodiments, the influenza virus grows to a titer of at least about 7.5 $\log_{10}$ PFU/ml in embryonated eggs and/or cell culture. In certain embodiments, the influenza virus grows to a titer of at least about 8 $\log_{10}$ PFU/ml in embryonated eggs and/or cell culture. In certain embodiments, the influenza virus grows to a titer of at least about 8.5 $\log_{10}$ PFU/ml in embryonated eggs and/or cell culture. In certain embodiments, the influenza virus grows to a titer of at least about 9 $\log_{10}$ PFU/ml in embryonated eggs and/or cell culture.

The methods of the invention can be advantageously used to produce recombinant and/or reassortant influenza viruses that exhibit increased replication capacity relative to parent strains. Such recombinant and/or reassortant viruses can be made, for example, by introducing a plurality of vectors collectively comprising nucleic acid sequences that express an infectious influenza viral particle into a population of host cells capable of supporting viral replication, as extensively described below. The host cells can be cultured under conditions permissive for viral growth, and influenza viruses recovered. In certain embodiments, the influenza viruses can be attenuated viruses, cold adapted viruses and/or temperature sensitive viruses. For example, in certain embodiments, the recombinant and/or reassortant influenza viruses can be attenuated, cold adapted, temperature sensitive viruses, such as are suitable for administration as a live attenuated vaccine, e.g., in a intranasal vaccine formulation.

For example, in some embodiments, the influenza viruses can be artificially engineered influenza viruses comprising one or more amino acid substitutions which increase influenza virus replication capacity. In certain embodiments, the influenza virus is a recombinant and/or reassortant influenza virus that comprises an M1 protein, wherein an amino acid of the M1 protein at a position corresponding to at least one of position 95, 143, 144, or 218 of the M1 protein of influenza strain MDV-A is altered. In certain embodiments, an amino acid at a position corresponding to at least one of position 95, 143, or 144 is altered. In certain embodiments, an amino acid at a position corresponding to at least one of position 95, 143, or 144 is altered and an amino acid at a position corresponding to position 218 is altered. In certain embodiments, the amino acid at the position corresponding to position 95 is altered to be lysine (K). In certain embodiments, the amino acid at the position corresponding to position 143 is altered to be alanine (A). In certain embodiments, the amino acid at the position corresponding to position 144 is altered to be phenylalanine (F). In certain embodiments, the amino acid at the position corresponding to position 218 is altered to be isoleucine (I). In certain embodiments, the amino acids at positions corresponding to each of positions 95, 143, 144 and 218 of the M1 protein of influenza strain MDV-A are altered. In addition, the influenza virus can include one or more additional amino acid alterations not enumerated above.

In certain embodiments, the replication capacity of the recombinant and/or reassortant influenza virus is increased at least 2-fold relative to the same recombinant and/or reassortant influenza virus in the absence of the alteration. In certain embodiments, the replication capacity of the recombinant and/or reassortant influenza virus is increased at least 4-fold relative to the same recombinant and/or reassortant influenza virus in the absence of the alteration. In certain embodiments, the replication capacity of the recombinant and/or reassortant influenza virus is increased at least 8-fold relative to the same recombinant and/or reassortant influenza virus in the absence of the alteration. In certain embodiments, the replication capacity of the recombinant and/or reassortant influenza virus is increased at least 10-fold relative to the same recombinant and/or reassortant influenza virus in the absence of the alteration.

In certain embodiments, the recombinant and/or reassortant influenza virus grows to a titer of at least about 7.5 $\log_{10}$ PFU/ml in embryonated eggs and/or cell culture. In certain embodiments, the recombinant and/or reassortant influenza virus grows to a titer of at least about 8 $\log_{10}$ PFU/ml in embryonated eggs and/or cell culture. In certain embodiments, the recombinant and/or reassortant influenza virus grows to a titer of at least about 8.5 $\log_{10}$ PFU/ml in embryonated eggs and/or cell culture. In certain embodiments, the recombinant and/or reassortant influenza virus grows to a titer of at least about 9 $\log_{10}$ PFU/ml in embryonated eggs and/or cell culture.

In certain embodiments, the recombinant and/or reassortant influenza virus comprises genomic segments 1, 2, 3, 5, and 8 from influenza strain MDV-A, genomic segment 7 from influenza strain A/Puerto Rico/8/34 (A/PR/8/34), and genomic segments 4 and 6 from any influenza strain known to one skilled in the art without limitation.

The recombinant and/or reassortant influenza viruses can be made by any method known to one skilled in the art without limitation. In some embodiments, a plurality of vectors collectively encoding at least the 6 internal genome segments (e.g., segments 1-3,5,7, and 8; "the backbone") of one or more influenza strains along with one or more genome segments encoding immunogenic influenza surface antigens of a different influenza strain can be introduced into a population of host cells. For example, at least the 6 internal genome segments of a selected influenza strain, for example, a strain including at least one of the M1 residues associated with increased replication capacity as described above can be introduced into a population of host cells along with one or more segments encoding immunogenic surface antigens derived from another virus strain. Typically the immunogenic surface antigens include either or both of the hemagglutinin (HA) and/or neuraminidase (NA) antigens. In embodiments where a single segment encoding an immunogenic surface antigen is introduced, the 7 complementary segments of the selected virus can be introduced into the host cells.

Further, the at least 6 internal genome segments can be selected to have one or more additional phenotypes as well. For example, the internal genome segments can be from a selected attenuated, cold adapted and/or temperature sensitive influenza strain, e.g., a ca, att, ts strain of A/Ann Arbor/6/60, B/Ann Arbor/1/66, or any other ca, att, and/or ts strain known to one skilled in the art without limitation.

In certain aspects, the invention provides an expression vector comprising a nucleic acid sequence operably linked to a pol I or pol II promoter, wherein the nucleic acid sequence encodes an influenza M1 protein comprising lysine (K) at position 95, alanine (A) at position 143, phenylalanine (F) at position 144, or isoleucine (I) at position 218, wherein the positions correspond to the M1 protein of influenza strain MDV-A. In certain embodiments, the nucleic acid sequence does not encode a wild-type M1 protein of influenza strain A/PR/8/34. In certain embodiments, the M1 protein comprises lysine (K) at position 95, alanine (A) at position 143, phenylalanine (F) at position 144, and isoleucine (I) at position 218.

In some embodiments, the expression vectors of the invention can be bi-directional expression vectors. A bi-directional expression vector of the invention typically includes a first promoter and a second promoter, wherein the first and second promoters are operably linked to alternative strands of the same double stranded cDNA encoding the viral nucleic acid comprising a segment of the influenza virus genome, e.g., a nucleic acid encoding an M1 protein. Preferably, one of the promoters is a RNA polymerase I promoter and the other promoter is an RNA polymerase II dependent promoter. The promoters are preferably able to initiate transcription in the cell into which the vector is to be introduced. Thus, for example, if the vector is to be introduced into a canine cell, a canine RNA pol I and/or RNA pol II promoter can be used. Optionally, the bi-directional expression vector also includes a polyadenylation signal and/or a terminator sequence. For example, the polyadenylation signal and/or the terminator sequence can be located flanking a segment of the influenza virus genome internal to the two promoters. One favorable polyadenylation signal in the context of the invention is the SV40 polyadenylation signal. An exemplary plasmid vector of the invention is the plasmid pAD3000.

Alternatively, the expression vectors of the invention can be unidirectional expression vectors. In a unidirectional vector system of the invention, the gene or cDNA encoding an influenza protein, e.g., an M1 protein associated with increased replication capacity as described herein, is located downstream of a pol I and a pol II promoter. The pol II promoter produces capped positive-sense viral mRNA and the pol I promoter produces uncapped positive-sense viral cRNA. The promoters are preferably able to initiate transcription in the cell into which the vector is to be introduced. Thus, for example, if the vector is to be introduced into a canine cell, a canine RNA pol I and/or RNA pol II promoter can be used. Optionally, the unidirectional expression vector also includes a polyadenylation signal and/or a terminator sequence. For example, the polyadenylation signal and/or the terminator sequence can be located flanking a segment of the influenza virus genome distal to the two promoters.

Whether bi-directional, unidirectional, or otherwise, the expression vectors can be introduced into host cells capable of supporting the replication of influenza virus from the vector promoters. Favorable examples of host cells include Vero cells, Per.C6 cells, BHK cells, PCK cells, MDCK cells, MDBK cells, 293 cells (e.g., 293T cells), and COS cells. In combination with the pAD3000 plasmid vectors described herein, Vero cells, 293 cells, and COS cells are particularly suitable. In some embodiments, co-cultures of a mixture of at least two of these cell lines, e.g., a combination of COS and MDCK cells or a combination of 293T and MDCK cells, constitute the population of host cells.

The host cells including the influenza vectors can then be grown in culture under conditions permissive for replication and assembly of viruses. In embodiments where cold adapted or temperature sensitive viruses are grown, host cells comprising the expression vectors of the invention can be cultured at a temperature below about 37° C., preferably at a temperature equal to, or less than, about 35° C. Typically, the cells are cultured at a temperature between about 32° C. and about 35° C. In some embodiments, the cells are cultured at a temperature between about 32° C. and 34° C., e.g., at about 33° C. Following culture for a suitable period of time to permit replication of the virus to high titer, recombinant and/or reassortant cold-adapted and/or temperature sensitive viruses can be recovered. Optionally, the recovered viruses can be inactivated.

In yet another aspect, the invention also provides broadly applicable methods of producing recombinant influenza viruses in cell culture by introducing a plurality of vectors collectively comprising nucleic acid sequences that express an infectious influenza viral particle, wherein one or more vectors encodes an M1 protein comprising one or more residues associated with increased replication capacity as described herein, into a population of host cells capable of supporting replication of influenza virus, culturing the cells, and recovering influenza viruses.

In certain embodiments, a plurality of expression vectors, e.g., plasmids, collectively comprising nucleic acid sequences that express an infectious influenza viral particle can be introduced into a population of host cells. In certain embodiments, eight expression vectors, each of which comprises a different influenza genomic segment, can be utilized to introduce a complete influenza genome into the host cells. The plasmid that encodes the M1 protein generally comprises one or more of the residues associated with increased replication capacity as described herein. Typically, the plasmid vectors of the invention are bi-directional expression vectors, as described above.

In some embodiments, the influenza viruses correspond to an influenza B virus. In some embodiments, the influenza viruses correspond to an influenza A virus. In certain embodiments, the methods include recovering recombinant and/or reassortant influenza viruses capable of eliciting an immune response upon administration, e.g., intranasal administration, to a subject. In some embodiments, the viruses are inactivated prior to administration. In other embodiments, live-attenuated viruses are administered. Recombinant and reassortant influenza A and influenza B viruses produced according to the methods of the invention are also contemplated according to the present invention.

In certain embodiments, the viruses made by the methods include an attenuated influenza virus, a cold adapted influenza virus, a temperature sensitive influenza virus, or a virus with any combination of these desirable properties, in addition to the increased replication capacity phenotype as described above. In one embodiment, the influenza virus comprises one or more proteins from an influenza B/Ann Arbor/1/66 strain virus, e.g., a cold adapted, temperature sensitive, attenuated strain of B/Ann Arbor/1/66. In another embodiment, the influenza virus comprises one or more proteins from an influenza A/Ann Arbor/6/60 strain virus, e.g., a cold adapted, temperature sensitive, attenuated strain of A/Ann Arbor/6/60. In certain embodiment of the invention, the viruses are artificially engineered influenza viruses comprising one or more substituted amino acid which increase the replication capacity of, e.g., ca A/Ann Arbor/6/60 or ca B/Ann Arbor/1/66. Such substituted amino acids can include one or more of amino acids corresponding to 95, 143, 144 and 218 of the M1 protein of influenza strain MDV-A. Any amino acid substitutions at any of these positions resulting in increased replication capacity are encompassed by the viruses and methods of the invention. It will be understood that some influenza A or B viruses may already have the recited residues at the indicated positions, e.g., 95K, 143A, 144F, and/or 218I. In this case, the substitutions can be used such that the resulting virus will have a substitution at positions 95, 143, 144, and 218.

Optionally, reassortant viruses are produced by introducing vectors collectively encoding the six internal genome segments of a viral strain selected for its favorable properties, in combination with the genome segments encoding the surface antigens (HA and NA) of a selected, e.g., pathogenic strain. For example, the HA segment can be selected from a pathogenically relevant H1, H3 or B strain, as is routinely performed for vaccine production. Similarly, the HA segment can be selected from an emerging pathogenic strain such as an H2 strain (e.g., H2N2), an H5 strain (e.g., H5N1) or an H7 strain (e.g., H7N7). Alternatively, the seven complementary gene segments of the first strain can be introduced in combination with either the HA or NA encoding segment. In certain embodiments, the internal gene segments are derived from the influenza B/Ann Arbor/1/66 or the A/Ann Arbor/6/60 strain. In certain embodiments, the internal gene segments, except for the gene segment encoding the M1 protein, are derived from the influenza B/Ann Arbor/1/66 or the A/Ann Arbor/6/60 strain, while the gene segment encoding the M1 protein is derived from the A/PR/8/34 strain. Alternately, the gene segment encoding the M1 protein can be derived from the influenza B/Ann Arbor/1/66 or the A/Ann Arbor/6/60 strain, wherein the M1 protein has been altered to encode one or more residues associated with increased replication capacity, as described herein.

Additionally, the invention provides methods for producing novel influenza viruses with desirable properties relevant to vaccine production, e.g., influenza viruses that exhibit increased replication capacity, as well as influenza vaccines including such novel influenza viruses. In certain embodiments, a novel influenza A strain virus can be produced by introducing mutations that result amino acid substitutions at one or more specified positions demonstrated herein to be important for the increased replication capacity phenotype, e.g., positions corresponding to position 95, 143, 144, or 218 of the M1 protein of influenza strain MDV-A. For example, mutations can be introduced at nucleotide positions resulting in an amino acid substitution at the specified amino acid position. Any mutation (at one or more of these positions) which individually or in combination results in increased replication capacity relative to wild type viruses is a suitable mutation in the context of the present invention.

To increase stability of the desired phenotype, a plurality of mutations can be typically introduced. Following introduction of the selected mutation(s) into the influenza genome, the mutated influenza genome can be replicated under conditions in which virus is produced. For example, the mutated influenza virus genome can be replicated in hens' eggs. Alternatively, the influenza virus genome can be replicated in cell culture. In the latter case, the virus can optionally be further amplified in hens' eggs to increase the titer. Viruses produced according to the methods of the invention are also a feature of the invention, as are vaccines including such viruses. Similarly, novel recombinant viral nucleic acids encoding an M1 protein having one or more mutations at positions corresponding to position 95, 143, 144, and/or 218 of the M1 protein of influenza strain MDV-A, and polypeptides with such amino acid substitutions are a feature of the invention.

Accordingly, in one aspect, the invention provides an isolated negative sense RNA expressed from an expression vector of the invention. In certain embodiments, the negative sense RNA encodes an influenza M1 protein comprising lysine (K) at position 95, alanine (A) at position 143, phenylalanine (F) at position 144, or isoleucine (I) at position 218, wherein the positions correspond to the M1 protein of influenza strain MDV-A. In certain embodiments, the negative sense RNA is not a wild-type genomic RNA from influenza strain A/PR/8/34.

In other aspects, the invention provides an influenza M1 protein comprising lysine (K) at position 95, alanine (A) at position 143, phenylalanine (F) at position 144, or isoleucine (I) at position 218, wherein the positions correspond to the M1 protein of influenza strain MDV-A. In certain embodiments, the protein is not a wild-type M1 protein of influenza strain A/PR/8/34.

In certain embodiments, the influenza M1 protein comprises lysine (K) at position 95, alanine (A) at position 143, phenylalanine (F) at position 144, and isoleucine (I) at position 218.

Moreover, influenza viruses comprising the mutations of the invention are a feature of the invention regardless of the method in which they are produced. That is, the invention encompasses influenza strains including the mutations of the invention, e.g., any influenza virus with an amino acid substitution relative to wild type at one or more positions selected from positions corresponding to positions 95, 143, 144, and 218 of the M1 protein of influenza strain MDV-A. In certain embodiments, the wild-type influenza virus is MDV-A or A/Wyoming/03/03.

Another aspect of the invention relates to novel methods for rescuing recombinant or reassortant influenza A or influenza B viruses (i.e., wild type and variant strains of influenza A and/or influenza viruses) having increased replication capacity in hens' eggs and/or cell culture as described herein from cells in culture. In such embodiments, a plurality of vectors collectively encoding an influenza virus genome, wherein the genome comprises a genomic segment encoding an M protein associated with increased replication capacity, can be introduced into a population of cells. The cells are grown under conditions permissive for viral replication, e.g., in the case of cold adapted, attenuated, temperature sensitive virus strains, the cells are grown at a temperature below 37° C., preferably at a temperature equal to, or less than, 35° C. Typically, the cells are cultured at a temperature between 32° C. and 35° C. In some embodiments, the cells are cultured at a temperature between about 32° C. and 34° C., e.g., at about 33° C. Optionally (e.g., for vaccine production), the cells are grown in serum free medium without any animal-derived products.

In the methods described above, influenza viruses having increased replication capacity can be recovered following culture of the host cells comprising the influenza genome plasmids. In some embodiments, the recovered influenza viruses having increased replication capacity are recombinant influenza viruses. In some embodiments, the viruses are reassortant influenza viruses having genetic contributions from more than one parental strain of virus. Optionally, the recovered recombinant or reassortant influenza viruses having increased replication capacity can be further amplified by passage in cultured cells or in hens' eggs.

Optionally, the recovered influenza viruses having increased replication capacity are inactivated. In some embodiments, the recovered influenza viruses comprise an influenza vaccine. For example, the recovered influenza vaccine can be a reassortant influenza viruses (e.g., 5:3, 6:2 or 7:1 reassortant viruses) having increased replication capacity and having an HA and/or NA antigen derived from a selected strain of influenza A or influenza B. In certain embodiments, the reassortant viruses have an increased replication capacity phenotype relative to at least one of the parent strains. In certain embodiments, the reassortant influenza viruses have an attenuated phenotype. Optionally, the reassortant viruses are cold adapted and/or temperature sensitive, e.g., an attenuated, cold adapted or temperature sensitive influenza virus. Such influenza viruses are useful, for example, as live attenuated vaccines for the prophylactic production of an immune response specific for a selected, e.g., pathogenic influenza strain. Influenza viruses, e.g., attenuated reassortant viruses, produced according to the methods of the invention are also contemplated according to the present invention.

In another aspect, the invention relates to methods for producing a recombinant influenza virus vaccine involving introducing a plurality of vectors collectively encoding an influenza virus genome, wherein the encoded M1 protein comprises one or more residues associated with increased replication capacity as described herein, into a population of host cells capable of supporting replication of influenza virus, culturing the host cells, and recovering an influenza virus capable of eliciting an immune response upon administration to a subject. The influenza vaccines of the invention can comprise either influenza A or influenza B strain viruses. In some embodiments, the influenza vaccine viruses include an influenza virus having increased replication capacity, an attenuated influenza virus, a cold adapted influenza virus, or a temperature sensitive influenza virus. In certain embodiments, the viruses possess a combination of these desirable properties. In an embodiment, the influenza virus contains an influenza A/Ann Arbor/6/60 strain virus with an altered M1 protein resulting in increased replication capacity. In another embodiment, the influenza virus comprises an influenza B/Ann Arbor/1/66 strain virus with an altered M1 protein resulting in increased replication capacity. Alternatively, the influenza vaccine includes artificially engineered influenza A or influenza B viruses comprising at least one substituted amino acid corresponding to at least one of positions 95, 143, 144, and 218 of the M1 protein of influenza strain MDV-A associated with increased replication capacity.

In some embodiments, the virus includes a reassortant influenza virus (e.g., a 5:3, 6:2 or 7:1 reassortant) having viral genome segments derived from more than one influenza virus strain. For example, a reassortant influenza virus vaccine favorably includes an HA and/or NA surface antigen derived from a selected strain of influenza A or B, in combination with the internal genome segments of one or more virus strain(s) selected for its desirable properties with respect to vaccine production. Often, it is desirable to select the strain of influenza from which the HA and/or NA encoding segments are derived based on predictions of local or world-wide prevalence of pathogenic strains. In some cases, the virus strain contributing at least some of the internal genome segments is an attenuated, cold adapted and/or temperature sensitive influenza strain, e.g., of A/Ann Arbor/6/60, B/Ann Arbor/1/66, or an artificially engineered influenza strain having one or more amino acid substitutions resulting in an attenuated, cold adapted and/or temperature sensitive phenotype. In such embodiments, the strain contributing the segment encoding the M1 protein is advantageously selected to be the A/PR/8/34 strain or an artificially engineered influenza strain having one or more amino acid substitutions resulting in an increased replication capacity phenotype, as described herein.

If desired, the influenza viruses, including influenza vaccine viruses, can be inactivated upon recovery.

Influenza virus vaccines, including attenuated live vaccines, produced by the methods of the invention are also contemplated according to the present invention. In certain embodiments the influenza virus vaccines are reassortant virus vaccines.

In yet another aspect, the invention provides kits including one or more expression vectors of the invention. Typically, the kits also include one or more of: a cell line capable of supporting influenza virus replication, a buffer, a culture medium, an instruction set, a packaging material, and a container. In some embodiments, the kit includes a plurality of expression vectors, each of which includes at least one segment of an influenza virus genome. For example, the kits can include a plurality of expression vectors each including one of the internal genome segments of a selected virus strain, e.g., each selected for its desirable properties with respect to vaccine production or administration. For example, the internal genome segments can independently be selected from a virus strain having an increased-replication capacity, attenuated, cold adapted and/or temperature sensitive strain, e.g., A/Ann Arbor/6/60, B/Ann Arbor/1/66, or A/PR/8/34, or an alternative strain with the desired properties, such as an artificially engineered strain having one or more amino acid substitutions as described herein. In one embodiment, the kit includes a expression vectors comprising members of a library of nucleic acids encoding variant HA and/or NA antigens.

The present invention also provides cell cultures including at least one cell comprising a plurality of vectors collectively comprising nucleic acid sequences that express an infectious influenza viral particle, wherein one or more of the vectors comprises a genomic segment encoding an M1 protein associated with increased replication capacity as described herein. The culture can also include a cell culture medium. In some embodiments, the plurality of vectors includes bi-directional expression vectors, e.g., comprising a first promoter inserted between a second promoter and an SV40 polyadenylation site as described above. For example, the first promoter and the second promoter can be situated in opposite orientations flanking at least one segment of an influenza virus. In some embodiments, e.g., when culturing a cold-adapted and/or temperature sensitive influenza virus, the cell cultures of the invention can be maintained at a temperature less than or equal to 35° C., such as between about 32° C. and 35° C., typically between about 32° C. and about 34° C., for example, at about 33° C.

In still another aspect, the invention provides a cell culture system that comprises a cell culture comprising at least one cell comprising a plurality of vectors collectively encoding a an influenza virus genome, as described above, and a regulator for maintaining the culture at a temperature less than or equal to 35° C. For example, in some embodiments, the regulator maintains the cell culture at a temperature between about 32° C. and 35° C., typically between about 32° C. and about 34° C., e.g., at about 33° C. Such embodiments are particularly useful for culturing, e.g., a temperature-sensitive and/or cold-adapted influenza virus.

In one embodiment, a method is provided for producing influenza viruses in cell culture, the method comprising: i) introducing a plurality of vectors collectively encoding an influenza virus genome into a population of host cells, wherein the influenza virus genome encodes an M1 protein that comprises one or more amino acids associated with increased replication capacity as described herein, and which population of host cells is capable of supporting replication of influenza virus; ii) culturing the population of host cells; and, iii) recovering a plurality of influenza viruses. In some embodiments, the a plurality of vectors comprise one or more genomic segments from an influenza B/Ann Arbor/1/66 virus. In some embodiments, the viral genome encodes an M1 protein that has lysine (K) at position 95, alanine (A) at position 143, phenylalanine (F) at position 144, or isoleucine (I) at position 218, where the positions correspond to the positions of influenza strain MDV-A.

In one embodiment, a method is provided for producing an influenza virus with increased replication capacity, the method comprising: (a) introducing into the segment encoding an M gene of an influenza virus genome at least one mutation at positions corresponding to positions 95, 143, 144, and/or 218 of the M1 protein of influenza strain MDV-A; and (b) replicating the mutated influenza virus genome under conditions whereby virus is produced. In some embodiments, the mutations encode lysine (K) at position 95, alanine (A) at position 143, phenylalanine (F) at position 144, and/or isoleucine (I) at position 218.

In one embodiment the invention provides methods for manipulating the amino acid residues of M1 to increase the ability of an influenza virus to replicate in embryonated hens' eggs and/or cell culture. In some embodiments, the method involves the introduction of amino acid residues substitutions in M1 and makes use of methods of producing influenza virus in cell culture by introducing a plurality of vectors collectively encoding an influenza virus genome into a population of host cells capable of supporting replication of influenza virus, culturing the cells and recovering influenza virus. Preferably, the recovered influenza virus has increased ability to replicate in embryonated hens' eggs and/or cell culture. In another embodiment, the present invention provides influenza virus variants with increased ability to replicate in embryonated hens' eggs and/or cell culture when compared to unmodified influenza viral strains.

5. BRIEF DESCRIPTION OF THE FIGURES

FIG. 1 presents the results of influenza plaque assays on MDCK cells showing the effects of the M segment on viral replication.

FIG. 2 presents an alignment of the M1 protein from several different influenza viral strains. M1 protein amino acid sequences shown are as follows: MDVA-M1 (SEQ ID NO:1), PR8-M (SEQ ID NO:2), Sendai-M1 (SEQ ID NO:3), SY97-M1 (SEQ ID NO:4), and WY03-M1 (SEQ ID NO:5).

FIG. 3 presents the results of influenza plaque assays on MDCK cells showing the effects of various site-directed mutations introduced into the M1 protein on replication in hens' eggs.

FIG. 4 presents the results of influenza plaque assays on MDCK cells showing the effects of various site-directed mutations introduced into the M1 protein on replication in hens' eggs.

6. DETAILED DESCRIPTION OF THE INVENTION

One substantial challenge in developing and producing influenza vaccines is that one or more of the circulating influenza strains may not replicate well in embryonic hens' eggs. The present invention identifies several amino acid residues which influence the activities of the M1 proteins and have identified specific amino acid substitutions which can modulate these activities. Thus, the present invention provides M1 proteins that can increase the replication capacity of influenza in eggs and/or host cells (e.g., Vero or MDCK cells). Specifically the present invention discloses amino acid substitutions and combinations of amino acid substitutions in M1 that can increase viral replication capacity in eggs and/or cell culture. Thus, the present invention provides, for example, for the use of reverse genetic technology to improve the manufacture of influenza virus vaccines.

In a first aspect, the methods of the invention provide vectors and methods for increasing the replication capacity of an influenza virus that comprises altering an amino acid at a position corresponding to at least one of position 95, 143, 144, or 218 of the M1 protein of influenza strain MDV-A, thereby increasing the replication capacity of the influenza virus. The vectors and methods are useful, for example, for making influenza viruses with increased replication capacity in e.g., hens' eggs and/or cell culture.

One skilled in the art will recognize that the exact position of the altered amino acid or amino acids can vary depending on the particular influenza strain used in the vectors, methods, and viruses of the invention. For example, the M1 protein of a particular influenza strain may comprise an insertion or deletion in the M gene encoding the M1 protein such that the position corresponding to position 95 of the M1 protein of MDV-A is found at, for example, residue 93 or 97 of the M1 protein of that particular influenza strain. One skilled in the art can readily recognize whether a particular amino acid position corresponds to a position that, when altered, is associated with increased replication capacity using techniques conventional to the art. One such conventional technique is to align the amino acid sequences of the M1 proteins of MDV-A and the particular influenza strain using algorithms available in the art. An example of such an alignment is shown in FIG. 2.

Exemplary algorithms that can be used to construct such alignments include, but are not limited to, the suite of BLAST programs, e.g., BLASTN, BLASTX, and TBLASTX, BLASTP and TBLASTN, using default parameters of an open gap penalty of 11.0, and an extended gap penalty of 1.0, and utilize the BLOSUM-62 matrix, which is publicly available on the Internet at the NCBI website, and the CLUSTAL-W program in MacVector version 6.5, operated with default parameters, including an open gap penalty of 10.0, an extended gap penalty of 0.1, and a BLOSUM 30 similarity matrix. See also Altschul et al., 1990, *J. Mol. Biol.* 215:403-10 (with special reference to the published default setting, i.e., parameters w=4, t=17) and Altschul et al., 1997, *Nucleic Acids Res.,* 25:3389-3402.

The influenza viruses can be produced, for example, by introducing a plurality of vectors comprising cloned influenza viral genomic segments into host cells, and culturing the cells. When vectors including an influenza virus genome are transfected, recombinant viruses suitable as vaccines can be recovered by standard purification procedures. Using the vector system and methods of the invention, reassortant viruses expressed from the six internal gene segments of a strain selected for its desirable properties with respect to vaccine production and/or viral replication, and from the immunogenic HA and NA segments from a selected, e.g., pathogenic strain, can be rapidly and efficiently produced in tissue culture. Thus, the system and methods described herein are useful for the rapid production in cell culture of recombinant and reassortant influenza A and B viruses, including viruses suitable for use as vaccines, including live attenuated vaccines, such as vaccines suitable for intranasal administration.

Typically, a single Master Donor Virus (MDV) strain is selected for each of the A and B subtypes. In the case of a live attenuated vaccine, the Master Donor Virus strain is typically chosen for its favorable properties, e.g., temperature sensitivity, cold adaptation, attenuation and/or increased replication capacity, relative to vaccine production. For example, exemplary Master Donor Strains include temperature sensitive, attenuated, cold adapted, and/or increased replication capacity strains of A/Ann Arbor/6/60 and B/Ann Arbor/1/66, respectively.

For example, a selected master donor type A virus (MDV-A), or master donor type B virus (MDV-B), can be produced from a plurality of cloned viral cDNAs encoding a viral genome. In an exemplary embodiment, recombinant viruses are produced from eight cloned viral cDNAs. Eight viral cDNAs representing either the selected MDV-A or MDV-B sequences of PB2, PB1, PA, NP, HA, NA, M and NS are cloned into a bi-directional expression vector, such as a plasmid (e.g., pAD3000), such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site).

Infectious recombinant MDV-A or MDV-B virus is then recovered following transfection of plasmids bearing the eight viral cDNAs into appropriate host cells, e.g., MDCK cells, Vero cells, co-cultured MDCK/293T or MDCK/COS7 cells. Using the plasmids and methods described herein, the invention is useful, e.g., for generating 6:2 reassortant influenza vaccines by co-transfection of the 6 internal genes (PB1, PB2, PA, NP, M and NS) of the selected virus (e.g., MDV-A, MDV-B) together with the HA and NA derived from different corresponding type (A or B) influenza viruses. Alternately, the plasmids and methods described herein can be used, e.g., for generating 5:3 reassortant influenza vaccines by co-transfection of 5 internal genes (PB1, PB2, PA, NP, and NS) of a selected virus (e.g., MDV-A, MDV-B) together with the M gene from different corresponding type (A or B) influenza viruses and HA and NA derived from the same or different corresponding type (A or B) influenza viruses as the virus from which the M gene is derived. For example, the HA segment can be selected from a pathogenically relevant H1, H3 or B strain, as is routinely performed for vaccine production. Similarly, the HA segment can be selected from a strain with emerging relevance as a pathogenic strain such as an H2 strain (e.g., H2N2), an H5 strain (e.g., H5N1) or an H7 strain (e.g., H7N7). Reassortants expressed from seven genome segments of the MDV and either the M, HA, or NA gene of a selected strain (7:1 reassortants) can also be produced. In addition, this system is useful for determining the molecular basis of phenotypic characteristics, e.g., the attenuated (att), cold adapted (ca), temperature sensitive (ts), and increased replication capacity (irc) phenotypes, relevant to vaccine production.

In another aspect the invention provides methods for manipulating the amino acid residues of M to increase the capacity for an influenza virus to replicate in embryonated hens' eggs and/or cell culture. For example, the methods of the present invention can be use to modulate M protein activity to increase the capacity of an influenza virus to replicate in eggs and/or cell culture as described herein. Additionally, the invention provides influenza viruses with increased capacity to replicate in embryonated hens' eggs and/or cell culture as described herein.

6.1 Definitions

Unless defined otherwise, all scientific and technical terms are understood to have the same meaning as commonly used in the art to which they pertain. For the purpose of the present invention the following terms are defined below.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one which regulates transcription in a specific tissue type or cell type, or types.

The term "vector" refers to a nucleic acid, e.g., a plasmid, viral vector, recombinant nucleic acid or cDNA that can be used to introduce heterologous nucleic acid sequences into a cell. The vectors can be autonomously replicating or not autonomously replicating. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are plasmids.

An "expression vector" is a vector, such as a plasmid, which is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is typically characterized by two alternative promoters oriented in the opposite direction relative to a nucleic acid situated between the two promoters, e.g., an RNA pol I promoter and an RNA pol II promoter, such that expression can be initiated in both orientations resulting in, e.g., transcription of both plus (+) or sense strand, and negative (−) or antisense strand RNAs. Alternatively, the bi-directional expression vector can be an ambisense vector, in which the viral mRNA and viral genomic RNA (as a cRNA) are expressed from the same strand.

A "unidirectional expression vector" is typically characterized by two alternative promoters oriented in the same direction relative to a nucleic acid operatively linked to the two promoters, e.g., an RNA pol I promoter and an RNA pol II promoter, such that expression can be initiated from both promoters resulting in, e.g., transcription of plus (+) strand RNAs. The plus strand RNA expressed from a pol I promoter can have defined ends suitable for use as, e.g., a viral cRNA. The plus strand RNA expressed from a pol I promoter can be capped, and, optionally, polyadenylated and is suitable for, e.g., translation of proteins encoded by the capped RNA.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "encode," in its various grammatical forms as used herein, refers to the ability of a first biological polymer, or collection of first biological polymers, to contain sequences that can be used to make other biological polymers having sequences defined by the first biological polymer(s). For example, a nucleic acid encodes a polypeptide when the nucleic acid comprises a sequence that, when translated, produces a polypeptide having a sequence defined by the nucleic acid sequence according to the conventional genetic code. In another example, a nucleic acid, or collection of nucleic acids, that encodes an influenza virus genome, can comprise the complete set of sequences necessary to express an infectious influenza particle. In another example, a negative-strand RNA that encodes a polypeptide can be used as a template for synthesis of positive-strand RNA that can be translated according to the genetic code to obtain the polypeptide.

The term "recombinant" indicates that the material (e.g., a nucleic acid or protein) has been artificially or synthetically (non-naturally) altered by human intervention. The alteration can be performed on the material within, or removed from, its natural environment or state. Specifically, when referring to a virus, e.g., an influenza virus, the virus is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus. A 5:3 reassortant includes 5 genomic segments, most commonly the PA, PB1, PB2, NP, and NS segments from a first parental virus, the M segment from a second parental virus, and the HA and NA segments from a third parental virus. Generally, at least one of the first, second, and third parental viruses can be different from the other two, or the first, second, and third parental viruses can each be different viruses.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." In the context of the invention a variety of methods can be employed to introduce nucleic acids into prokaryotic cells, including electroporation, calcium phosphate precipitation, lipid mediated transfection (lipofection), etc.

The term "host cell" means a cell which contains a heterologous nucleic acid, such as a vector, and supports the replication and/or expression of the nucleic acid, and optionally production of one or more encoded products including a polypeptide and/or a virus. Host cells can be prokaryotic cells such as *E. coli*, or eukaryotic cells such as yeast, insect, amphibian, avian or mammalian cells, including human cells. Exemplary host cells in the context of the invention include Vero (African green monkey kidney) cells, Per.C6 cells (human embryonic retinal cells), BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells). The term host cell encompasses combinations or mixtures of cells including, e.g., mixed cultures of different cell types or cell lines (e.g., Vero and CEK cells). A co-cultivation of electroporated sf vero cells is described, for example, in PCT/US04/42669 filed Dec. 22, 2004, which is incorporated by reference in its entirety.

The terms "temperature sensitive," "cold adapted" and "attenuated" are well known in the art and are used herein according to their ordinary meanings. For example, the term "temperature sensitive" ("ts") can indicate that the virus exhibits a 100 fold or greater reduction in titer at 39° C. relative to 33° C. for influenza A strains, and/or that the virus exhibits a 100 fold or greater reduction in titer at 37° C. relative to 33° C. for influenza B strains. For example, the term "cold adapted" ("ca") can indicate that the virus exhibits growth at 25° C. within 100 fold of its growth at 33° C. For example, the term "attenuated" ("att") can indicate that the virus replicates in the upper airways of ferrets but is not detectable in lung tissues, and/or does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses in some embodiments of the invention. Growth can indicate viral quantity as indicated by titer, plaque size or morphology, particle density or other measures known to those of skill in the art.

The term "increased replication capacity," as used herein with reference to a viral phenotype, means that the virus grows to a greater titer in an appropriate medium, e.g., an embryonated hens' egg or cell culture, relative to a parent virus. For example, a 7:1 or 5:3 reassortant virus that has an M segment that results in a greater titer of virus grown relative to an virus with an M segment from one of the parent strains has an "increased replication capacity" phenotype. In another example, a virus that has been altered in its M gene to encode amino acids that result in a greater titer of virus relative to a parent virus that has not been altered in its M gene also has an "increased replication capacity" phenotype.

The expression "artificially engineered" is used herein to indicate that the virus, viral nucleic acid or virally encoded product, e.g., a polypeptide, a vaccine, comprises at least one mutation introduced by recombinant methods, e.g., site directed mutagenesis, PCR mutagenesis, etc. The expression "artificially engineered" when referring to a virus (or viral component or product) comprising one or more nucleotide mutations and/or amino acid substitutions indicates that the viral genome or genome segment encoding the virus (or viral component or product) is not derived from naturally occurring sources, such as a naturally occurring or previously existing laboratory strain of virus produced by non-recombinant methods (such as progressive passage at 25° C.), e.g., a wild type or cold adapted A/Ann Arbor/6/60 or B/Ann Arbor/1/66strain.

The term "about," as used herein, unless otherwise indicated, refers to a value that is no more than 10% above or below the value being modified by the term. For example, the term "about 5 μg/kg" means a range of from 4.5 μg/kg to 5.5 μg/kg. As another example, "about 1 hour" means a range of from 48 minutes to 72 minutes.

The term "encode," as used herein, refers to the property of a nucleic acid, e.g., deoxyribonucleic acid, to transcribe a complementary nucleic acid, including a nucleic acid that can be translated into a polypeptide. For example, a deoxyribonucleic acid can encode an RNA that is transcribed from the deoxyribonucleic acid. Similarly, the deoxyribonucleic acid can encode a polypeptide translated from an RNA transcribed from the deoxyribonucleic acid.

6.2 Methods for Enhancing Viral Replication Capacity

In one aspect, the present invention provides a method of increasing the capacity of an influenza virus to replicate in embryonated hens' eggs and/or host cells. Generally, the methods comprise use of an M1 protein comprising one or more amino acid residues associated with increased replication capacity as described herein. The invention further provides influenza virus variants with increased ability to replicate in embryonated hens' eggs and/or host cells when compared to influenza virus with an M protein that does not comprise the one or more amino acids associated with increased replication capacity. It is specifically contemplated that the methods of the invention can be utilized to increase the replication capacity of an influenza virus in a hen egg and/or cell culture and that increased replication capacity variants may have increased replication capacity in hens' eggs and/or host cells. Suitable host cells for the replication of influenza virus include, e.g., Vero cells, Per.C6 cells, BHK cells, MDCK cells, 293 cells and COS cells, including 293T cells and COS7 cells.

In one embodiment, the method of the invention introduces at least one amino acid substitution into an M protein which will increase the ability of an influenza virus to replicate in eggs and/or host cells by at least about 10%, or by at least about 20%, or by at least about 30%, or by at least about 40%, or by at least about 50%, or by at least about 60%, or by at least about 70%, or by at least about 80%, or by at least about 90%, or by at least about 100%, or by at least about 200%, or by at least about 300%, or by at least about 400%, or by at least about 500% when compared to the unmodified influenza virus. Preferably, the method of the invention does not significantly alter the antigenicity of the substituted influenza virus when compared to the unsubstituted virus. In a specific embodiment, the method of the invention reduces the antigenicity of the substituted influenza virus when compared to the unsubstituted virus by less then 10%, or by less then 20%, or by less then 30%, or by less then 40%, or by less then 50%, or by less then 60%, or by less then 70%, or by less then 80%, or by less then 90%, or by less then 100%. Methods to determine viral antigenicity are well known in the art.

In one embodiment, the method of the invention further encompasses an attenuated influenza virus, a cold adapted influenza virus, a temperature sensitive influenza virus, or a virus with any combination of these desirable properties. Preferably, the viruses encompassed by the method of the invention include but are not limited to, influenza B/Ann Arbor/1/66 strain virus, influenza A/Ann Arbor/6/60 strain virus. In another embodiment, the method of the invention introduces vectors including the six internal genes of a viral strain selected for its favorable properties regarding vaccine production, e.g., an attenuated, cold adapted, temperature sensitive, and/or increased replication capacity strain, in combination with the genome segments encoding the desired HA and NA surface antigens to produce influenza viruses with increased ability to replicate in embryonated hens' eggs and/or host cells and the desired antigenicity provided by the selected HA and NA. In another embodiment, the method of the invention further comprises making and/or using a non-attenuated influenza virus.

In certain embodiments, the method introduces at least one amino acid substitution in the M1 protein at positions corresponding to positions 95, 143, 144, or 218 of the M1 protein. In one embodiment, amino acid substitutions are made at positions 143 and 144 or at positions 95 and 218 or at positions 95 and 143, or at positions 95 and 144, or at positions 143 and 218, or at positions 144 and 218, or at positions 95, 143, and 144, or at positions 95, 143, and 218, or at positions 95, 144, and 218, or at positions 143, 144, and 218, or at positions 95, 143, 144 and 218. In certain embodiments, the amino acid at the position corresponding to position 95 is altered to be lysine (K). In certain embodiments, the amino acid at the position corresponding to position 143 is altered to be alanine (A). In certain embodiments, the amino acid at the position corresponding to position 144 is altered to be phenylalanine (F). In certain embodiments, the amino acid at the position corresponding to position 218 is altered to be isoleucine (I). In another specific embodiment, the changes at these positions can be made such that a conservative amino acid change is made with respect to the changes described above.

One skilled in the art would appreciate that in some cases the M1 protein will already have the altered amino acid residues at one or more of the aforementioned positions. In this situation, substitution(s) can be introduced at any of the remaining non-matching positions.

It is specifically contemplated that conservative amino acid substitutions may be made for said amino acid substitutions at positions 95, 143, 144 and/or 218 of M1, described supra.

It is well known in the art that "conservative amino acid substitution" refers to amino acid substitutions that substitute functionally-equivalent amino acids. For example, one or more amino acids of a similar polarity can act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Families of conservative amino acid substitutions include but are not limited to, non-polar (e.g., Trp, Phe, Met, Leu, Ile, Val, Ala, Pro), uncharged polar (e.g., Gly, Ser, Thr, Asn, Gln, Tyr, Cys), acidic/negatively charged (e.g., Asp, Glu), basic/positively charged (e.g., Arg, Lys, His), beta-branched (e.g., Thr, Val, Ile), residues that influence chain orientation (e.g., Gly, Pro) and aromatic (e.g., Trp, Tyr, Phe, His). The term "conservative amino acid substitution" also refers to the use of amino acid analogs or variants. Guidance concerning how to make phenotypically silent amino acid substitutions is provided in Bowie et al., 1990, *Science* 247: 1306-10.

In one embodiment, a method of increasing the replication capacity of a reassortant influenza virus by at least about 10% is provided wherein the method comprises the steps of: a) comparing the amino acid sequence of the reassortant influenza virus with the amino acid sequence of a different influenza virus that replicates to a higher titer in embryonated eggs and/or cell culture; and b) altering one or more amino acid of the sequence of the reassortant virus to match the sequence of the different influenza virus, thereby producing one or more altered reassortant viruses, and c) growing the one or more altered reassortant virus in eggs and/or cell culture. In some embodiments, the amino acid sequence is the sequence of an M protein, e.g., an M1 protein or an M2 protein. Influenza viruses produced by these methods are also an embodiment of the invention.

In another specific embodiment, a method of increasing the replication capacity of an influenza virus by at least 10% or at least 20% or at least 50% or at least 80% is provided, the method comprising the steps of: a) making amino acid substitutions as needed at one or more of the following M1 positions: 95, 143, 144, or 218, such that such substitution, if made, results in a valine residue at position 95, an alanine at position 143, a phenylalanine at position 144, and an threonine at position 218, and b) growing the influenza virus comprising the M1 substitutions in eggs and/or cell culture. Immunogenic compositions and vaccines comprising the influenza viruses of the invention are also provided. In further embodiments, the method further comprises making amino acid substitutions at positions 143 and 144 or at positions 95 and 218 or at positions 95 and 143, or at positions 95 and 144, or at positions 143 and 218, or at positions 144 and 218, or at positions 95, 143, and 144, or at positions 95, 143, and 218, or at positions 95, 144, and 218, or at positions 143, 144, and 218, or at positions 95, 143, 144 and 218.

6.2.1. Methods for Manipulation of Viral Nucleic Acids and Proteins

In the context of the invention, nucleic acids encoding M proteins with substitutions associated with increased replication capacity, expression vectors, influenza virus nucleic acids and/or proteins and the like can be manipulated according to well known molecular biology techniques. Detailed protocols for numerous such procedures, including amplification, cloning, mutagenesis, transformation, and the like, are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies including mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (Midland, Tex.), The Great American Gene Company (Salt Lake City, Utah), ExpressGen, Inc. (Chicago, Ill.), Operon Technologies, Inc. (Huntsville, Ala.), and many others.

In addition, substitutions of selected amino acid residues in viral polypeptides can be accomplished by, e.g., site directed mutagenesis. For example, viral polypeptides with amino acid substitutions functionally correlated with desirable phenotypic characteristic, e.g., an attenuated phenotype, cold adaptation, temperature sensitivity, can be produced by introducing specific mutations into a viral nucleic acid segment encoding the polypeptide. Methods for site directed mutagenesis are well known in the art, and described, e.g., in Ausubel, Sambrook, and Berger, supra. Numerous kits for performing site directed mutagenesis are commercially available, e.g., the Chameleon Site Directed Mutagenesis Kit (Stratagene, La Jolla), and can be used according to the manufacturers instructions to introduce, e.g., one or more amino acid substitutions, into a genome segment encoding an influenza A or B polypeptide, respectively.

6.3 Influenza Viruses with Increased Replication Capacity

In addition, the present invention further provides influenza viruses with increased replication capacity. Generally, the influenza viruses with increased replication capacity are recombinant and/or reassortant influenza viruses comprising an M1 protein with amino acid substitutions associated with increased replication capacity as described herein. Such viruses can be made, for example, according to the methods described above.

Accordingly, in certain embodiments, the invention provides an influenza virus that comprises an M1 protein, wherein an amino acid of the M1 protein at a position corresponding to at least one of position 95, 143, 144, or 218 of the M1 protein of influenza strain MDV-A is altered. In certain embodiments, the amino acid at the position corresponding to position 95 is altered to be lysine (K). In certain embodiments, the amino acid at the position corresponding to position 143 is altered to be alanine (A). In certain embodiments, the amino acid at the position corresponding to position 144 is altered to be phenylalanine (F). In certain embodiments, the amino acid at the position corresponding to position 218 is altered to be isoleucine (I). In certain embodiments, the amino acids at positions corresponding to each of positions 95, 143, 144 and 218 of the M1 protein of influenza strain MDV-A are altered. In addition, the influenza virus can include one or more additional amino acid alterations not enumerated above.

In certain embodiments, the replication capacity of the reassortant and/or recombinant influenza virus is increased at least about 10%, or at least about 20%, or at least about 30%, or at least about 40%, or at least about 50%, or at least about 60%, or at least about 70%, or at least about 80%, or at least about 90%, or at least about 100%, or at least about 200%, or at least about 300%, or at least about 400%, or at least about 500% when compared to the unmodified influenza virus.

In certain embodiments, the replication capacity of the reassortant and/or recombinant influenza virus is increased at least 2-fold relative to the same reassortant and/or recombinant influenza virus in the absence of the alteration. In certain embodiments, the replication capacity of the reassortant and/or recombinant influenza virus is increased at least 4-fold relative to the same reassortant and/or recombinant influenza virus in the absence of the alteration. In certain embodiments, the replication capacity of the reassortant and/or recombinant influenza virus is increased at least 8-fold relative to the same reassortant and/or recombinant influenza virus in the absence of the alteration. In certain embodiments, the replication capacity of the reassortant and/or recombinant influenza virus is increased at least 10-fold relative to the same reassortant and/or recombinant influenza virus in the absence of the alteration.

In certain embodiments, the reassortant influenza virus grows to a titer of at least about 7.5 $\log_{10}$ PFU/ml in embryonated eggs and/or cell culture. In certain embodiments, the reassortant influenza virus grows to a titer of at least about 8 $\log_{10}$ PFU/ml in embryonated eggs and/or cell culture. In certain embodiments, the reassortant influenza virus grows to a titer of at least about 8.5 $\log_{10}$ PFU/ml in embryonated eggs and/or cell culture. In certain embodiments, the reassortant influenza virus grows to a titer of at least about 9 $\log_{10}$ PFU/ml in embryonated eggs and/or cell culture.

In certain embodiments, the reassortant influenza virus comprises genomic segments 1, 2, 3, 5, and 8 from influenza strain MDV-A, genomic segment 7 from influenza strain A/PR/8/34, and genomic segments 4 and 6 from any influenza strain known to one skilled in the art without limitation.

In certain embodiments, the invention provides an influenza virus comprising at least one amino acid substitution in the M1 protein at a position corresponding to positions 95, 143, 144, or 218 of the M1 protein. In one embodiment, the M1 protein comprises a substitution at positions 143 and 144, at positions 95 and 218, at positions 95 and 143, at positions 95 and 144, at positions 143 and 218, at positions 144 and 218, at positions 95, 143, and 144, at positions 95, 143, and 218, at positions 95, 144, and 218, at positions 143, 144, and 218, or at positions 95, 143, 144 and 218. In certain embodiments, the amino acid at the position corresponding to position 95 is altered to be lysine (K). In certain embodiments, the amino acid at the position corresponding to position 143 is altered to be alanine (A). In certain embodiments, the amino acid at the position corresponding to position 144 is altered to be phenylalanine (F). In certain embodiments, the amino acid at the position corresponding to position 218 is altered to be isoleucine (I). In another specific embodiment, the changes at these positions can be made such that a conservative amino acid change is made with respect to the changes described above.

One skilled in the art would appreciate that in some cases the M1 protein will already have the altered amino acid residues at one or more of the aforementioned positions. In this situation, the M1 protein can comprise one or more substitution(s) at any of the remaining non-matching positions.

It is specifically contemplated that conservative amino acid substitutions may be made for said amino acid substitutions at positions 95, 143, 144 and/or 218 of M1, described supra.

In one embodiment, the present invention provides modified influenza viruses which comprise at least one amino acid substitution in M1 which increases their replication capacity in embryonated hens' eggs and/or host cells when compared to the unmodified influenza virus. Preferably, the ability of an influenza variant having increased replication capacity to replicate in eggs and/or host cells has been increased by at least 10%, or by at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% when compared to the unmodified influenza virus.

In certain embodiment, an influenza variant having increased replication capacity further encompasses an attenuated influenza virus, a cold adapted influenza virus, a temperature sensitive influenza virus, or a virus with any combination of these desirable properties. Preferably, the viruses that can be made into influenza variants having increased replication capacity include, but are not limited to, influenza B/Ann Arbor/1/66 strain viruses or influenza A/Ann Arbor/6/60 strain viruses. It is specifically contemplated that an influenza variants having increased replication capacity can be produced by introducing vectors including the six internal genes of a viral strain selected for its favorable properties regarding vaccine production, in combination with the genome segments encoding the desired substituted HA and NA surface antigens.

In another specific embodiment, the invention includes reassortant influenza viruses comprising a substitution at one or more of the following positions: 95, 143, 144, or 218, wherein the influenza virus grows to a titer of at least 8.0 $\log_{10}$ PFU/ml, or at least 8.5 $\log_{10}$ PFU/ml, or least 9.0 $\log_{10}$ PFU/ml in embryonated eggs and/or cell culture. Immunogenic compositions and vaccines comprising the influenza viruses of the invention are also provided.

In another specific embodiment, the invention includes reassortant influenza viruses comprising a substitution at one or more of the following positions: 95, 143, 144, or 218, wherein the influenza virus grows to a titer at least 50% higher, or at least 80% higher, or at least 100% higher than the same reassortant virus not having the substitution made.

6.4 Nucleic Acids Encoding Influenza M1 Proteins Associated with Increased Replication Capacity In another aspect, the invention provides nucleic acids encoding an influenza protein that is associated with increased replication capacity. The nucleic acids typically encode an M1 protein having amino acid residues associated with increased replication capacity as described herein.

Accordingly, in certain embodiments, the invention provides an isolated nucleic acid that encodes an M1 protein, wherein an amino acid of the M1 protein at a position corresponding to at least one of position 95, 143, 144, or 218 of the M1 protein of influenza strain MDV-A is altered relative to a parent nucleic acid. In certain embodiments, the amino acid at the position corresponding to position 95 is altered to be lysine (K). In certain embodiments, the amino acid at the position corresponding to position 143 is altered to be alanine (A). In certain embodiments, the amino acid at the position corresponding to position 144 is altered to be phenylalanine (F). In certain embodiments, the amino acid at the position corresponding to position 218 is altered to be isoleucine (I). In certain embodiments, nucleic acid encodes an M1 protein wherein each of the amino acids at positions corresponding to positions 95, 143, 144 and 218 of the M1 protein of influenza strain MDV-A are altered relative to the parent nucleic acid.

In certain embodiments, the nucleic acid is DNA. In certain embodiments, the nucleic acid is RNA.

In certain embodiments, the nucleic acid encodes an M1 protein comprising at least one amino acid substitution at a position corresponding to positions 95, 143, 144, or 218 of the M1 protein. In one embodiment, the M1 protein comprises a substitution at positions 143 and 144, at positions 95 and 218, at positions 95 and 143, at positions 95 and 144, at positions 143 and 218, at positions 144 and 218, at positions 95, 143, and 144, at positions 95, 143, and 218, at positions 95, 144, and 218, at positions 143, 144, and 218, or at positions 95, 143, 144 and 218. In certain embodiments, the amino acid at the position corresponding to position 95 is altered to be lysine (K). In certain embodiments, the amino acid at the position corresponding to position 143 is altered to be alanine (A). In certain embodiments, the amino acid at the position corresponding to position 144 is altered to be phenylalanine (F). In certain embodiments, the amino acid at the position corresponding to position 218 is altered to be isoleucine (I). In another specific embodiment, the substitution(s) at these positions can be made such that a conservative amino acid change is made with respect to the changes described above.

One skilled in the art would appreciate that in some cases the M1 protein encoded by the nucleic acid will already have the altered amino acid residues at one or more of the aforementioned positions. In this situation, the M1 protein can comprise one or more substitution(s) at any of the remaining non-matching positions.

It is specifically contemplated that conservative amino acid substitutions may be made in the nucleic acid encoding any of the amino acid substitutions at positions corresponding to positions 95, 143, 144 and/or 218 of the M1 protein of MDV-A.

6.5 Vectors for Making Influenza Viruses

In another aspect, the invention provides vectors that comprise a nucleic acid of the invention, including expression vectors useful for recombinantly rescuing a virus from cell culture. Generally, the expression vectors are useful, for example, for rescuing an influenza virus in cell culture. Typically, at least one of the expression vectors will encode an influenza M1 protein that comprises one or more amino acid residues associated with increased replication capacity as described herein.

In accordance with the present invention, in one embodiment, cDNA encoding viral genomic RNA corresponding to each of the eight genomic segments of influenza (segments may be from different influenza viruses, e.g., 6 from strain X and 2 from strain Y, or 5 from strain X, 2 from strain Y, and 1 from strain Z) can be inserted into a recombinant vector for manipulation and production of influenza viruses. A variety of vectors, including viral vectors, plasmids, cosmids, phage, and artificial chromosomes, can be employed in the context of the invention. Typically, for ease of manipulation, the cDNA is inserted into a plasmid vector, providing one or more origins of replication functional in bacterial and eukaryotic cells, and, optionally, a marker convenient for screening or selecting cells comprising the plasmid sequence. See, e.g., Neumann et al., 1999, *PNAS*. USA 96:9345-9350.

In one embodiment, the vectors of the invention are bidirectional expression vectors capable of initiating transcription of a viral genomic segment from the inserted cDNA in either direction, that is, giving rise to both (+) strand and (−) strand viral RNA molecules. To effect bi-directional transcription, each of the viral genomic segments is inserted into an expression vector having at least two independent promoters, such that copies of viral genomic RNA are transcribed by a first RNA polymerase promoter (e.g., an RNA pol I promoter), from one strand, and viral mRNAs are synthesized from a second RNA polymerase promoter (e.g., an RNA Pol II promoter). Accordingly, the two promoters can be arranged in opposite orientations flanking at least one cloning site (i.e., a restriction enzyme recognition sequence) preferably a unique cloning site, suitable for insertion of viral genomic RNA segments. Alternatively, an "ambisense" expression vector can be employed in which the (+) strand mRNA and the (−) strand viral RNA (as a cRNA) are transcribed from the same strand of the vector.

To ensure the correct 3' end of each expressed vRNA or cRNA, each vRNA or cRNA expression vector can comprise a ribozyme sequence or appropriate termination sequence (e.g., human, mouse, primate, or canine RNA polymerase I termination sequence) downstream of the RNA coding sequence. This may be, for example, the hepatitis delta virus genomic ribozyme sequence or a functional derivative thereof, or the murine rDNA termination sequence (Genbank Accession Number M12074). Alternatively, for example, a pol I termination sequence may be employed (Neumann et al., 1994, Virology 202:477-479). The RNA expression vectors may be constructed in the same manner as the vRNA expression vectors described in Pleschka et al., 1996, J. Virol. 70:4188-4192; Hoffmann and Webster, 2000, J. Gen Virol. 81:2843-2847; Hoffmann et al., 2002, Vaccine 20:3165-3170; Fodor et al., 1999, J. Virol. 73:9679-9682; Neumann et al., 1999, P.N.A.S. USA 96:9345-9350; and Hoffmann et al., 2000, Virology 267:310-317, each of which is hereby incorporated by reference in its entirety.

In another embodiment, the vectors are unidirectional expression vectors, wherein viral cDNA is inserted between a pol I promoter and a termination sequences (inner transcription unit). This inner transcription unit is flanked by an RNA polymerase II (pol II) promoter and a polyadenylation site (outer transcription unit). In the unidirectional system, the pol I and pol II promoters are upstream of the cDNA and produce positive-sense uncapped cRNA (from the pol I promoter) and positive-sense capped mRNA (from the pol II promoter. See, e.g., Hoffmann and Webster, 2000, *J. Gen. Virol.* 81:2843-2847.

In other systems, viral sequences transcribed by the pol I and pol II promoters can be transcribed from different expression vectors. In these embodiments, vectors encoding each of the viral genomic segments under the control of a pol I promoter ("vRNA expression vectors") and vectors encoding one or more viral polypeptides, e.g., influenza PA, PB1, PB2, and NP polypeptides ("protein expression vectors") under the control of a pol II promoter can be used.

In either case, with regard to the pol II promoter, the influenza virus genome segment to be expressed can be operably linked to an appropriate transcription control sequence (promoter) to direct mRNA synthesis. A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, and polyoma virus, and various retroviral promoters. Mammalian promoters include, among many others, the actin promoter, immunoglobulin promoters, heat-shock promoters, and the like. In a specific embodiment, the regulatory sequence comprises the adenovirus 2 major late promoter linked to the spliced tripartite leader sequence of human adenovirus 2, as described by Berg et al., Bio Techniques 14:972-978. In addition, bacteriophage promoters can be employed in conjunction with the cognate RNA polymerase, e.g., the T7 promoter.

Expression vectors used to express viral proteins, in particular viral proteins for RNP complex formation, will preferably express viral proteins homologous to the desired virus. The expression of viral proteins by these expression vectors may be regulated by any regulatory sequence known to those of skill in the art. The regulatory sequence may be a constitutive promoter, an inducible promoter or a tissue-specific promoter. Further examples of promoters which may be used to control the expression of viral proteins in protein expression vectors include, but are not limited to, the SV40 early promoter region (Bernoist and Chambon, 1981, Nature 290: 304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (VIIIa-Kamaroff et al., 1978, Proc. Natl. Acad. Sci. USA 75:3727-3731), or the tac promoter (DeBoer et al., 1983, Proc. Natl. Acad. Sci. USA 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus $^{35}$S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, protein expression vectors of the invention comprise a promoter operably linked to a nucleic acid sequence, one or more origins of replication, and, optionally, one or more selectable markers (e.g., an antibiotic resistance gene). In another embodiment, a protein expression vector of the invention that is capable of producing bicistronic mRNA may be produced by inserting bicistronic mRNA sequence. Certain internal ribosome entry site (IRES) sequences may be utilized. Preferred IRES elements include, but are not limited to the mammalian BiP IRES and the hepatitis C virus IRES.

In one embodiment, a nucleic acid of the invention is inserted into plasmid pAD3000 or a derivative thereof. See, U.S. patent application publication US2005/0266026, hereby incorporated by reference in its entirety. Thus, in certain embodiments, the expression vector is a bi-directional expression vector. In certain embodiments, the expression vector comprises a SV40 polyadenylation signal flanking a segment of the influenza virus genome internal to the two promoters. In certain embodiments, the expression vector comprises the cytomegalovirus (CMV) DNA dependent RNA Pol II promoter.

Vectors containing gene inserts can be identified by, e.g., three general approaches: (a) nucleic acid hybridization; (b) presence or absence of "marker" gene functions; and, in the case of expression vectors, (c) expression of inserted sequences. In the first approach, the presence of the viral gene inserted in an vector(s) can be detected by nucleic acid hybridization using probes comprising sequences that are homologous to the inserted gene(s). In the second approach, the recombinant vector/host system can be identified and selected based upon the presence or absence of certain "marker" gene functions (e.g., resistance to antibiotics or transformation phenotype) caused by the insertion of the gene(s) in the vector(s). In the third approach, expression vectors can be identified by assaying the gene product expressed. Such assays can be based, for example, on the physical or functional properties of the viral protein in in vitro assay systems, e.g., binding of viral proteins to antibodies.

In a specific embodiment, one or more protein expression vectors encode and express the viral proteins necessary for the formation of RNP complexes. In another embodiment, one or more protein expression vectors encode and express the viral proteins necessary to form viral particles. In yet another embodiment, one or more protein expression vectors encode and express the all of the viral proteins of a particular negative-strand RNA virus.

Transcription from expression vectors can optionally be increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha.-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) *Heat stress promoters and transcription factors Results Probl Cell Differ*

20:125-62; Kriegler et al. (1990) *Assembly of enhancers, promoters, and splice signals to control expression of transferred genes Methods in Enzymol* 185: 512-27). Optionally, the amplicon can also contain a ribosome binding site or an internal ribosome entry site (IRES) for translation initiation.

The expression vectors of the invention can also include sequences for the termination of transcription and for stabilizing the mRNA, such as a polyadenylation site or a termination sequence (e.g., human, mouse, primate, or canine RNA polymerase I termination sequence). Such sequences are commonly available from the 5' and, occasionally 3', untranslated regions of eukaryotic or viral DNAs or cDNAs. In some embodiments, the SV40 polyadenylation sequences provide a polyadenylation signal.

In addition, as described above, the vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The expression vector containing the appropriate DNA sequence as described above, as well as an appropriate promoter or control sequence, can be employed to transform a host cell permitting expression of the protein. While the expression vectors of the invention can be replicated in bacterial cells, most frequently it will be desirable to introduce them into mammalian cells, e.g., Vero cells, BHK cells, MDCK cell, 293 cells, or COS cells, or co-cultures thereof, for the purpose of expression.

The expression vectors of the invention can be used to directing the expressing of genomic vRNA(s) or corresponding cRNA(s) which have one or more mutations (e.g., removal or inactivation of a polybasic cleavage site in the HA gene of particular influenza pandemic strains such as H5N1). These mutations may result in the attenuation of the virus. For example, the vRNA segments may be the vRNA segments of an influenza A virus having an attenuated base pair substitution in a pan-handle duplex promoter region, in particular, for example, the known attenuating base pair substitution of A for C and U for G at position 11-12' in the duplex region of the NA-specific vRNA (Fodor et al., 1998, J. Virol. 6923-6290).

Most commonly, the genome segment encoding the influenza virus protein further includes any additional sequences necessary for its expression, including translation into a functional viral protein. In other situations, a minigene, or other artificial construct encoding the viral proteins, e.g., an HA or NA or M1 protein, can be employed. In this case, it is often desirable to include specific initiation signals which aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually in-frame with the polynucleotide sequence of interest, e.g., to target polypeptide expression to a desired cellular compartment, membrane, or organelle, or into the cell culture media. Such sequences are known to those of skill in the art, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Finally, any of the vectors described in U.S. Pat. Nos. 6,951,754, 6,887,699, 6,649,372, 6,544,785, 6,001,634, 5,854,037, 5,824,536, 5,840,520, 5,820,871, 5,786,199, and 5,166,057 and U.S. Patent Application Publication Nos. 20060019350, 20050158342, 20050037487, 20050266026, 20050186563, 20050221489, 20050032043, 20040142003, 20030035814, and 20020164770, for example, can be used in accordance with the present invention. Generally, the vectors described in these publications can be adapted for use in accordance with the present invention by introducing a nucleic acid of the invention (e.g., a nucleic acid encoding an influenza M1 protein with substitutions associated with increased replication capacity as described herein) into expression vectors to direct synthesis of viral vRNA or cRNA.

The expression vectors can also be used to make chimeric viruses having increased replication capacity that express sequences heterologous to a viral genome. In such embodiments, expression vectors directing the expression of vRNA(s) or corresponding cRNA(s) can be introduced into host cells along with expression vectors directing the expression of viral proteins, including an M1 protein comprising residues associated with increased replication capacity, to generate novel infectious recombinant negative-strand RNA viruses or chimeric viruses. See, e.g., US patent application publication no. US2004/0002061. Heterologous sequences which may be engineered into these viruses include, for example, antisense nucleic acids and a nucleic acid such as a ribozyme. Alternatively, heterologous sequences which express a peptide or polypeptide may be engineered into these viruses. Heterologous sequences encoding the following peptides or polypeptides may be engineered into these viruses include: 1) antigens that are characteristic of a pathogen; 2) antigens that are characteristic of autoimmune disease; 3) antigens that are characteristic of an allergen; and 4) antigens that are characteristic of a tumor. For example, heterologous gene sequences that can be engineered into the chimeric viruses of the invention include, but are not limited to, epitopes of human immunodeficiency virus (HIV) such as gp160; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

Antigens that are characteristic of autoimmune disease typically will be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discoid lupus erythromatosus.

Antigens that are allergens are generally proteins or glycoproteins, including antigens derived from pollens, dust, molds, spores, dander, insects and foods.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within an negative-strand RNA virus gene coding sequence such that a chimeric gene product is expressed which contains the heterologous peptide sequence within the viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

One approach for constructing these hybrid molecules is to insert the heterologous coding sequence into a DNA complement of a negative-strand RNA virus gene so that the heterologous sequence is flanked by the viral sequences required for viral polymerase activity; e.g., an RNA pol I promoter and a polyadenylation site. In an alternative approach, oligonucleotides encoding an RNA pol I promoter, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82:488). Variations in polymerase chain reaction (PCR) technology, described, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophase T3, T7 or SP6) and the hybrid sequence containing the heterologous gene and a canine RNA pol I promoter. RNA templates could then be transcribed directly from this recombinant DNA. In yet another embodiment, the recombinant vRNAs or corresponding cRNAs may be prepared by ligating RNAs specifying the negative polarity of the heterologous gene and the canine RNA pol I promoter using an RNA ligase.

Bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with virus packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology with picornaviral elements. Preferred IRES elements include, but are not limited to the mammalian BiP FRES and the hepatitis C virus IRES.

Alternatively, a foreign protein may be expressed from an internal transcriptional unit in which the transcriptional unit has an initiation site and polyadenylation site. In another embodiment, the foreign gene is inserted into a negative-strand RNA virus gene such that the resulting expressed protein is a fusion protein.

6.6 Viral Propagation in Cell Culture

The present invention further contemplates that influenza viruses having influenza viruses having increased replication capacity may be grown in cell culture, as extensively described below.

6.6.1. Cells and Cell Cultures for Growing Influenza Viruses

Any host cell known to one skilled in the art to be useful for culturing influenza viruses may be used in accordance with the present invention. Host cells are preferably animal cells, more preferably mammalian cells, and most preferably canine cells. Host cells which may be used to generate the negative-strand RNA viruses of the invention include primary cells, cultured or secondary cells, and transformed or immortalized cells (e.g., 293 cells, 293T cells, CHO cells, Vero cells, PK, MDBK, OMK and MDCK cells). In some embodiments, influenza viruses having increased replication capacity are generated in MDCK cells.

Typically, propagation of the virus can be accomplished in the media compositions in which the host cell is commonly cultured. Suitable host cells for the replication of influenza virus include, e.g., Vero cells, Per.C6 cells, BHK cells, MDCK cells, 293 cells and COS cells, including 293T cells and COS7 cells. Co-cultures including two of the above cell lines, e.g., MDCK cells and either 293T or COS cells can also be employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Suitable serum free media are described, for example, in U.S. Provisional Application No. 60/638,166, filed Dec. 23, 2004, and in U.S. Provisional Application No. 60/641,139, filed Jan. 5, 2005, each of which is hereby incorporated by reference in its entirety. Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) *Culture of Animal Cells: Manual of Basic Technique*, Alan R. Liss, New York; Paul (1975) *Cell and Tissue Culture*, $5^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine*

*preparation*. In Cohen and Shafferman (eds) *Novel Strategies in Design and Production of Vaccines*, which is incorporated herein in its entirety. Additionally, variations in such procedures adapted to the present invention are readily determined through routine experimentation.

Cells for production of influenza virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

6.6.2. Methods for Growing Influenza Viruses in Cell Culture

The present invention further provides methods of generating infectious recombinant influenza viruses having increased replication capacity by introducing protein expression vectors and vRNA or corresponding cRNA expressing expression vectors of the invention into host cells in the absence of helper virus. The present invention also provides methods of generating infectious recombinant influenza viruses having increased replication capacity by introducing protein expression vectors and vRNA or corresponding cRNA expressing expression vectors of the invention into host cells in the presence of helper virus. In either case, recombinant influenza viruses having increased replication capacity can be generated using vectors encoding an M1 protein with residues associated with increased replication capacity as described herein.

Protein expression vectors and expression vectors directing the expression of vRNAs or corresponding cRNAs can be introduced into host cells using any technique known to those of skill in the art without limitation. For example, expression vectors of the invention can be introduced into host cells by employing electroporation, DEAE-dextran, calcium phosphate precipitation, liposomes, microinjection, and microparticle-bombardment (see, e.g., Sambrook et al., Molecular Cloning: A Laboratory Manual, 2 ed., 1989, Cold Spring Harbor Press, Cold Spring Harbor, N.Y.). The expression vectors may be introduced into host cells simultaneously or sequentially.

In one embodiment, one or more expression vectors directing the expression of vRNA(s) or corresponding cRNA(s) are introduced into host cells prior to the introduction of expression vectors directing the expression of viral proteins. In another embodiment, one or more expression vectors directing the expression of viral proteins are introduced into host cells prior to the introduction of the one or more expression vectors directing the expression of vRNA(s) or corresponding cRNA(s). In accordance with these embodiments, the expression vectors directing the expression of the vRNA(s) or corresponding cRNA(s) may introduced together or separately in different transfections. Further, in accordance with these embodiments, the expression vectors directing the expression of the viral proteins can be introduced together or separately in different transfections.

In another embodiment, one or more expression vectors directing the expression of vRNA(s) or corresponding cRNA(s) and one or more expression vectors directing the expression of viral proteins are introduced into host cells simultaneously. In certain embodiments, all of the expression vectors are introduced into host cells using liposomes.

Appropriate amounts and ratios of the expression vectors for carrying out a method of the invention may be determined by routine experimentation. As guidance, in the case of liposomal transfection or calcium precipitation of plasmids into the host cells, it is envisaged that each plasmid may be employed at a few μgs, e.g., 1 to 10 μg, for example, diluted to a final total DNA concentration of about 0.1 μg/ml prior to mixing with transfection reagent in conventional manner. It may be preferred to use vectors expressing NP and/or RNA-dependent RNA polymerase subunits at a higher concentration than those expressing vRNA segments. One skilled in the art will appreciate that the amounts and ratios of the expression vectors may vary depending upon the host cells.

In one embodiment, at least 0.5 μg, preferably at least 1 μg, at least 2.5 μg, at least 5 μg, at least 8 μg, at least 10 μg, at least 15 μg, at least 20 μg, at least 25 μg, or at least 50 μg of one or more protein expression vectors of the invention are introduced into host cells to generate infectious recombinant negative-strand RNA virus. In another embodiment, at least 0.5 μg, preferably at least 1 μg, at least 2.5 μg, at least 5 μg, at least 8 μg, at least 10 μg, at least 15 μg, at least 20 μg, at least 25 μg or at least 50 μg of one or more expression vectors of the invention directing the expression of vRNAs or cRNAs are introduced into host cells to generate infectious influenza viruses.

The present invention further provides methods of generating infectious recombinant influenza viruses having increased replication capacity in stably transduced host cell lines. The stably transduced host cell lines of the invention may be produced by introducing cDNA encoding, inter alia, an influenza M1 protein having residues associated with increased replication capacity, controlled by appropriate expression control elements (e.g., promoter, enhancer, sequences, transcription termination sequences, polyadenylation sites, etc.), and a selectable marker into host cells. Following the introduction of the foreign DNA, the transduced cells may be allowed to grow for 1-2 days in an enriched media, and then are switched to a selective media. The selectable marker confers resistance to the cells and allows the cells to stably integrate the DNA into their chromosomes. Transduced host cells with the DNA stably integrated can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

The infectious recombinant influenza viruses generated by methods of the invention which are not attenuated, may be attenuated or killed by, for example, classic methods. For example, recombinant influenza viruses of the invention may be killed by heat or formalin treatment, so that the virus is not capable of replicating. Recombinant influenza viruses of the invention which are not attenuated may be attenuated by, e.g., passage through unnatural hosts to produce progeny viruses which are immunogenic, but not pathogenic.

Attenuated, live or killed viruses produced in accordance with the invention may subsequently be formulated into a vaccine composition in conventional manner or used to produce additional virus, e.g., in eggs. Where such a virus has a chimeric vRNA segment as discussed above which encodes a foreign antigen, it may be formulated to achieve vaccination against more than one pathogen simultaneously. Attenuated recombinant viruses produced in accordance with the invention which possess a chimeric vRNA segment may also be designed for other therapeutic uses, e.g., an anti-tumor agent or gene therapy tool, in which case production of the virus will be followed by its incorporation into an appropriate pharmaceutical composition together with a pharmaceutically acceptable carrier or diluent.

Helper virus free rescue in accordance with the invention is particularly favored for generation of reassortant influenza viruses, especially reassortant influenza viruses desired for vaccine use particularly since selection methods are not needed to rid the culture of helper virus.

The methods of the present invention may be modified to incorporate aspects of methods known to those skilled in the art, in order to improve efficiency of rescue of infectious viral particles. For example, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoprotein (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in U.S. Pat. No. 5,789,229 issued Aug. 4, 1998; in European Patent Publication EP 0702085A1, published Feb. 20, 1996; in U.S. patent application Ser. No. 09/152,845; in International Patent Publications PCR WO97/12032 published Apr. 3, 1997; WO96/34625 published Nov. 7, 1996; in WO99/02657 published Jan. 21, 1999; WO98/53078 published Nov. 26, 1998; WO98/02530 published Jan. 22, 1998; WO99/15672 published Apr. 1, 1999; WO98/13501 published Apr. 2, 1998; WO97/06720 published Feb. 20, 1997; and EPO 780 475 published Jun. 25, 1997, each of which is incorporated by reference herein in its entirety.

The present invention further provides a method for generating in cultured cells an infectious recombinant influenza virus, such as an influenza A or B virus, said method comprising: (a) introducing into a population of cells capable of supporting growth of said virus a first set of expression vectors capable of expressing in said cells genomic vRNA segments to provide the complete genomic vRNA segments of said virus, wherein the genomic vRNA segment encoding the M1 protein encodes an M1 protein having one or more residues associated with increased replication capacity as described herein; (b) introducing into said cells a second set of expression vectors capable of expressing mRNA encoding one or more polypeptides of said virus; and (c) culturing said cells whereby infectious influenza viral particles are produced. In certain embodiments, the recombinant virus is influenza A or B virus. In certain embodiments, the first set of expression vectors comprises 1-8 plasmids. In certain embodiments, the first set of expression vectors comprises one plasmid. In certain embodiments, the second set of expression vectors comprises 1-8 plasmids. In certain embodiments, the second set of expression vectors comprises one plasmid. In certain embodiments, the first, second, or both sets of expression vectors are introduced by electroporation. In certain embodiments, the first set of expression vectors encode each vRNA segment of an influenza virus. In certain embodiments, the second set of expression vectors encode the mRNA of one or more or all influenza polypeptides. In certain embodiments, the first set or second set of expression vectors (or both sets) encode a vRNA or mRNA of a second virus. For instance, a set of vectors can comprise one or more vectors encoding the HA and/or NA mRNA and/or vRNA of a second influenza virus. In one embodiment, helper virus is used in the method.

The present invention further provides a method for generating in cultured cells infectious recombinant influenza viruses, such as an influenza A or B virus, said method comprising: (a) introducing into a population of cells capable of supporting growth of said virus a set of expression vectors capable of both expressing in said cells genomic vRNA segments to provide the complete genomic vRNA segments of said virus and of expressing mRNA encoding one or more polypeptides of said virus, wherein the genomic vRNA segment encoding the M1 protein encodes an M1 protein having one or more residues associated with increased replication capacity as described herein; and (b) culturing said cells whereby viral particles are produced. In certain embodiments, the influenza virus is influenza A or B virus. In certain embodiments, the set of expression vectors comprises 1-17 plasmids. In certain embodiments, the set of expression vectors comprises 1-8 plasmids. In certain embodiments, the set of expression vectors comprises 1-3 plasmids. In certain embodiments, the set of expression vectors comprises one plasmid. In certain embodiments, the sets of expression vectors are introduced by electroporation. In certain embodiments, the set of expression vectors encode each vRNA segment of an influenza virus. In certain embodiments, the set of expression vectors encode the mRNA of one or more influenza polypeptides. In certain embodiments, the set of expression vectors encode each vRNA segment of an influenza virus and the mRNA of one or more influenza polypeptides. In certain embodiments, the set of expression vectors comprise a nucleic acid of the invention, for example, a nucleic acid encoding an influenza M1 protein having one or more residues associated with increased replication capacity as described herein. In certain embodiments, the set of expression vectors encode a vRNA or mRNA of a second virus. For instance, in some embodiments, the set of vectors can comprise one or more vectors encoding the HA and/or NA mRNA and/or vRNA of a second influenza virus. In certain embodiments, the first set or second set of expression vectors (or both sets) encode a vRNA or mRNA of a second virus. For instance, in some embodiments, a set of vectors can comprise one or more vectors encoding the HA and/or NA mRNA and/or vRNA of a second influenza virus. In one embodiment, helper virus is used in the method. In other embodiments, a set of vectors can comprise one or more vectors encoding the M1 of a second influenza virus, e.g., an M1 protein associated with increased replication capacity as described herein or an M1 protein from a A/PR/8/34 influenza virus.

The present invention further provides a method for generating in cultured cells infectious recombinant influenza viral particles, said method comprising: (a) introducing into a population of cells capable of supporting growth of said virus a first set of expression vectors capable of expressing in said cells genomic vRNA to provide the complete genomic vRNA of said virus, wherein the genomic vRNA segment encoding the M1 protein encodes an M1 protein having one or more residues associated with increased replication capacity as described herein; (b) introducing into said cells a second set of expression vectors capable of expressing mRNA encoding one or more polypeptides of said virus; and (c) culturing said cells whereby said viral particles are produced. In certain embodiments, the cells are canine cells. In certain embodiments, the cells are MDCK cells. In certain embodiments, the virus is influenza A or B virus. In certain embodiments, the first set of expression vectors comprises 1-8 plasmids. In certain embodiments, the first set of expression vectors comprises one plasmid. In certain embodiments, the second set of expression vectors comprises 1-8 plasmids. In certain embodiments, the second set of expression vectors comprises one plasmid. In certain embodiments, the first, second, or both sets of expression vectors are introduced by electroporation. In certain embodiments, the first set of expression vectors encode each vRNA segment of an influenza virus. In certain embodiments, the second set of expression vectors encode the mRNA of one or more influenza polypeptides. In certain embodiments, the first set or second set of expression vectors (or both sets) comprise a nucleic acid of the invention, for example, a nucleic acid encoding an influenza M1 protein having one or more residues associated with increased replication capacity as described herein. In one embodiment, helper virus is used in the method. In one embodiment, the cultured cells used in the method are canine cells.

The present invention further provides a method for generating in cultured cells infectious viral particles of an influenza virus, said method comprising: (a) introducing into a population of cells capable of supporting growth of said virus a set of expression vectors capable of both expressing in said cells genomic vRNA to provide the complete genomic vRNA of said virus and expressing mRNA encoding one or more polypeptides of said virus, wherein the genomic vRNA segment encoding the M1 protein encodes an M1 protein having one or more residues associated with increased replication capacity as described herein; and (b) culturing said cells whereby said viral particles are produced. In certain embodiments, the cells are canine cells. In certain embodiments, the cells are MDCK cells. In certain embodiments, the virus is am influenza A or B virus. In certain embodiments, the set of expression vectors comprises 1-17 plasmids. In certain embodiments, the set of expression vectors comprises 1-8 plasmids. In certain embodiments, the set of expression vectors comprises 1-3 plasmids. In certain embodiments, the set of expression vectors is introduced by electroporation. In certain embodiments, the set of expression vectors encode each vRNA segment of an influenza virus. In certain embodiments, the set of expression vectors encode the mRNA of one or more influenza polypeptides. In certain embodiments, the set of expression vectors encode each vRNA segment of an influenza virus and the mRNA of one or more influenza polypeptides. In certain embodiments, the set of expression vectors comprise a nucleic acid of the invention, for example, a nucleic acid encoding an influenza M1 protein having one or more residues associated with increased replication capacity as described herein. In certain embodiments, the set of expression vectors encode a vRNA or mRNA of a second virus. For instance, in some embodiments, the set of vectors can comprises one or more vectors encoding the HA and/or NA and/or M1 mRNA and/or vRNA of a second influenza virus. In one embodiment, helper virus is used in the method. In one embodiment, the cultured cells used in the method are canine cells.

In a specific embodiment, the present invention provides for methods of generating infectious recombinant influenza virus in host cells using expression vectors to express the vRNA segments or corresponding cRNAs and influenza virus proteins, in particular PB1, PB2, PA and NA. In accordance with this embodiment, helper virus may or may not be included to generate the infectious recombinant influenza viruses.

The infectious recombinant influenza viruses of the invention may or may not replicate and produce progeny. Preferably, the infectious recombinant influenza viruses of the invention are attenuated. Attenuated infectious recombinant influenza viruses may, for example, have a mutation in the NS1 gene.

In certain embodiments, an infectious recombinant influenza virus of the invention can be used to produce other viruses useful to prepare a vaccine composition of the invention. In one embodiment, recombinant or reassortant influenza viruses produced by a method of the invention are used for the production of additional virus for use as a vaccine. For example, a population of recombinant or reassortant viruses having increased replication capacity can be produced by the methods of the invention as described above. Subsequently, the population of viruses can be grown in eggs or another culture such that additional viruses are produced for the preparation of vaccines or an immunogenic composition.

In certain embodiments, the infectious recombinant influenza viruses of the invention express heterologous (i.e., non-influenza virus) sequences, as described above. In another embodiment, the infectious recombinant influenza viruses of the invention express influenza virus proteins from different influenza strains. In yet another embodiment, the infectious recombinant influenza viruses of the invention express fusion proteins.

6.6.3. Methods for Recovering Influenza Viruses from Cell Culture

Viruses can typically be recovered from the culture medium, in which infected (transfected) cells have been grown. Typically crude medium is clarified prior to concentration of influenza viruses. Common methods include filtration, ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 μm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. *Vaccine Production*, in Nicholson et al. (eds) *Textbook of Influenza* pp. 324-332; Merten et al. (1996) *Production of influenza virus in cell cultures for vaccine preparation*, in Cohen & Shafferman (eds) *Novel Strategies in Design and Production of Vaccines* pp. 141-151, and U.S. Pat. No. 5,690,937, U.S. publication application nos. 20040265987, 20050266026 and 20050158342, which are incorporated by reference herein. If desired, the recovered viruses can be stored at −80° C. in the presence of sucrose-phosphate-glutamate (SPG) as a stabilizer.

6.7 Influenza Vaccines

Historically, influenza virus vaccines have been produced in embryonated hens' eggs using strains of virus selected based on empirical predictions of relevant strains. More recently, reassortant viruses have been produced that comprise selected hemagglutinin and neuraminidase antigens in the context of an approved attenuated, temperature sensitive master strain. Following culture of the virus through multiple passages in hens' eggs, influenza viruses are recovered and, optionally, inactivated, e.g., using formaldehyde and/or β-propiolactone. However, production of influenza vaccine in this manner has several significant drawbacks. Among these drawbacks are the inability of certain circulating influenza strains to replicate to high titer in hens' eggs, thus limiting the amount of vaccine that can be made from the eggs.

The present invention provides a vector system, compositions, and methods for producing recombinant and reassortant viruses that have increased replication capacity in eggs and/or culture which make it possible to produce vaccines corresponding to one or many selected antigenic strains of virus. In particular, conditions and strains are provided that result in efficient production of viruses from a multi plasmid system in cell culture. Optionally, if desired, the viruses can be further amplified in hens' eggs or cell cultures that differ from the cultures used to rescue the virus.

Reassortant influenza viruses can be readily obtained by introducing a subset of vectors comprising cDNA that encodes genomic segments of a master influenza virus, in combination with complementary segments derived from strains of interest (e.g., antigenic variants of interest). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. In this context, influenza A strain ca A/Ann Arbor/6/60; influenza B strain ca B/Ann Arbor/1/66; or another strain selected for its desirable phenotypic properties, e.g., an attenuated, cold adapted, and/or temperature sensitive strain, are favorably selected as master donor strains.

In one embodiment, plasmids comprising cDNA encoding the six internal vRNA segments of the influenza master virus strain, (i.e., PB1, PB2, PA, NP, NB, M1, BM2, NS1 and NS2) are transfected into suitable host cells in combination with cDNA encoding hemagglutinin and neuraminidase vRNA segments from an antigenically desirable strain, e.g., a strain predicted to cause significant local or global influenza infection. Following replication of the reassortant virus in cell, reassortant viruses are recovered. Optionally, if desired, the viruses can be further amplified in hens' eggs or cell cultures that differ from the cultures used to rescue the virus. Optionally, the recovered virus can be inactivated using a denaturing agent such as formaldehyde or β-propiolactone.

6.7.1. Vaccine Compositions

The present invention further provides compositions comprising an influenza virus of the invention. Such compositions can comprise, for example, recombinant and reassortant viruses in an appropriate carrier or excipient. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected hens' eggs (i.e., normal allantoic fluid "NAF") or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

6.7.2. Methods of Administering Vaccine Compositions

Generally, the influenza viruses of the invention are administered in a quantity sufficient to stimulate an immune response specific for one or more strains of influenza virus. Preferably, administration of the influenza viruses elicits a protective immune response. Dosages and methods for eliciting a protective immune response against one or more influenza strains are known to those of skill in the art. For example, inactivated influenza viruses are provided in the range of about 1-1000 $HID_{50}$ (human infectious dose), i.e., about $10^5$-$10^8$ pfu (plaque forming units) per dose administered. Alternatively, about 10-50 μg, e.g., about 15 μg HA can be administered without an adjuvant, with smaller doses being administered with an adjuvant. Typically, the dose can be adjusted within this range based on, e.g., age, physical condition, body weight, sex, diet, time of administration, and other clinical factors. The prophylactic vaccine formulation can be systemically administered, e.g., by subcutaneous or intramuscular injection using a needle and syringe, or a needleless injection device. Alternatively, the vaccine formulation can be administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect.

Alternatively, an immune response can be stimulated by ex vivo or in vivo targeting of dendritic cells with influenza viruses. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

Optionally, the formulation for prophylactic administration of the influenza viruses, or subunits thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1, B7.2, etc. The immunostimulatory molecules can be administered in the same formulation as the influenza viruses, or can be administered separately. Either the protein or an expression vector encoding the protein can be administered to produce an immunostimulatory effect.

In another embodiment, the vectors of the invention including influenza genome segments can be employed to introduce heterologous nucleic acids into a host organism or host cell, such as a mammalian cell, e.g., cells derived from a human subject, in combination with a suitable pharmaceutical carrier or excipient as described above. Typically, the heterologous nucleic acid is inserted into a non-essential region of a gene or gene segment, e.g., the M gene of segment 7. The heterologous polynucleotide sequence can encode a polypeptide or peptide, or an RNA such as an antisense RNA or ribozyme. The heterologous nucleic acid can then be introduced into a host or host cells by producing recombinant viruses comprising the heterologous nucleic acid, and the viruses are administered as described above. In one embodiment, the heterologous polynucleotide sequence is not derived from an influenza virus.

Alternatively, a vector of the invention including a heterologous nucleic acid can be introduced and expressed in a host cells by co-transfecting the vector into a cell infected with an influenza virus. Optionally, the cells are then returned or delivered to the subject, typically to the site from which they were obtained. In some applications, the cells are grafted onto a tissue, organ, or system site (as described above) of interest, using established cell transfer or grafting procedures. For example, stem cells of the hematopoietic lineage, such as bone marrow, cord blood, or peripheral blood derived hematopoietic stem cells can be delivered to a subject using standard delivery or transfusion techniques.

Alternatively, the viruses comprising a heterologous nucleic acid can be delivered to the cells of a subject in vivo. Typically, such methods involve the administration of vector particles to a target cell population (e.g., blood cells, skin cells, liver cells, neural (including brain) cells, kidney cells, uterine cells, muscle cells, intestinal cells, cervical cells, vaginal cells, prostate cells, etc., as well as tumor cells derived from a variety of cells, tissues and/or organs. Administration can be either systemic, e.g., by intravenous administration of viral particles, or by delivering the viral particles directly to a site or sites of interest by a variety of methods, including injection (e.g., using a needle or syringe), needleless vaccine delivery, topical administration, or pushing into a tissue, organ or skin site. For example, the viral vector particles can be delivered by inhalation, orally, intravenously, subcutaneously, subdermally, intradermally, intramuscularly, intraperitoneally, intrathecally, by vaginal or rectal administration, or by placing the viral particles within a cavity or other site of the body, e.g., during surgery.

The above described methods are useful for therapeutically and/or prophylactically treating a disease or disorder by introducing a vector of the invention comprising a heterologous polynucleotide encoding a therapeutically or prophylactically effective polypeptide (or peptide) or RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors." Optionally, more than one heterologous coding sequence is introduced into a single vector or virus. For example, in addition to a polynucleotide encoding a therapeutically or prophylactically active polypeptide or RNA, the vector can also include additional therapeutic or prophylactic polypeptides, e.g., antigens, co-stimulatory molecules, cytokines, antibodies, etc., and/or markers, and the like.

In one embodiment, the invention provides compositions comprising reassortant and recombinant viruses of the invention (or portions thereof) that have been treated with an agent such as benzonase, to eliminate potential oncogenes. Accordingly, an oncogene-free vaccine composition is specifically included within the embodiments of the invention.

The methods and vectors of the present invention can be used to therapeutically or prophylactically treat a wide variety of disorders, including genetic and acquired disorders, e.g., as vaccines for infectious diseases, due to viruses, bacteria, and the like.

6.8 Specific Embodiments

Additional embodiments of the present invention are presented in Table 1.

TABLE 1

| | Specific embodiments |
|---|---|
| 1 | A method for increasing the replication capacity of an influenza virus, comprising altering an amino acid at a position corresponding to at least one of position 95, 143, 144 or 218 of the M1 protein of influenza strain MDV-A, thereby increasing the replication capacity of the influenza virus, with the proviso that the amino acid corresponding to position 218 is not altered to be a threonine (T). |
| 2 | The method of embodiment 1, wherein an amino acid corresponding to at least two of positions 95, 143, 144, or 218 are altered. |
| 3 | The method of embodiment 1, wherein an amino acid corresponding to at least three of positions 95, 143, 144, or 218 are altered. |
| 4 | The method of embodiment 1, wherein the amino acid at the position corresponding to position 95 is altered. |
| 5 | The method of embodiment 4, wherein the amino acid at the position corresponding to position 95 is altered to be lysine (K). |
| 6 | The method of embodiment 1, wherein the amino acid at the position corresponding to position 143 is altered. |

TABLE 1-continued

| Specific embodiments | |
|---|---|
| 7 | The method of embodiment 6, wherein the amino acid at the position corresponding to position 143 is altered to be alanine (A). |
| 8 | The method of embodiment 1, wherein the amino acid at the position corresponding to position 144 is altered. |
| 9 | The method of embodiment 8, wherein the amino acid at the position corresponding to position 144 is altered to be phenylalanine (F). |
| 10 | The method of embodiment 1, wherein the amino acid at the position corresponding to position 218 is altered. |
| 11 | The method of embodiment 10, wherein the amino acid at the position corresponding to position 218 is altered to be isoleucine (I). |
| 12 | A method for increasing the replication capacity of an influenza virus, comprising altering amino acids at positions corresponding to positions 95, 143, 144 and 218 of the M1 protein of influenza strain MDV-A, thereby increasing the replication capacity of the influenza virus. |
| 13 | The method of embodiment 12, wherein the amino acid at the position corresponding to position 95 is altered to be lysine (K). |
| 14 | The method of embodiment 4, wherein the amino acid at the position corresponding to position 143 is altered to be alanine (A). |
| 15 | The method of embodiment 4, wherein the amino acid at the position corresponding to position 144 is altered to be phenylalanine (F). |
| 16 | The method of embodiment 4, wherein the amino acid at the position corresponding to position 218 is altered to be isoleucine (I). |
| 17 | The method of embodiment 4, wherein the amino acid at the position corresponding to position 95 is altered to be lysine (K), the amino acid at the position corresponding to position 143 is altered to be alanine (A), the amino acid at the position corresponding to position 144 is altered to be phenylalanine (F) and the amino acid at the position corresponding to position 218 is altered to be isoleucine (I). |
| 18 | The method of embodiment 1 or 12, wherein the replication capacity of the influenza virus is increased at least 2-fold relative to the same influenza virus in the absence of the alteration. |
| 19 | The method of embodiment 1 or 12, wherein the replication capacity of the influenza virus is increased at least 4-fold relative to the same influenza virus in the absence of the alteration. |
| 20 | The method of embodiment 1 or 12, wherein the replication capacity of the influenza virus is increased at least 8-fold relative to the same influenza virus in the absence of the alteration. |
| 21 | The method of embodiment 1 or 12, wherein the replication capacity of the influenza virus is increased at least 10-fold relative to the same influenza virus in the absence of the alteration. |
| 22 | The method of embodiment 1 or 12, wherein the influenza virus grows to a titer of at least about 7.5 log10 PFU/ml in embryonated eggs. |
| 23 | The method of embodiment 1 or 12, wherein the influenza virus grows to a titer of at least about 8 log10 PFU/ml in embryonated eggs. |
| 24 | The method of embodiment 1 or 12, wherein the influenza virus grows to a titer of at least about 8.5 log10 PFU/ml in embryonated eggs. |
| 25 | The method of embodiment 1 or 12, wherein the influenza virus grows to a titer of at least about 9 log10 PFU/ml in embryonated eggs. |
| 26 | A reassortant influenza virus comprising an M1 protein, wherein an amino acid of the M1 protein at a position corresponding to at least one of position 95, 143, 144, or 218 of the M1 protein of influenza strain MDV-A is altered. |
| 27 | The reassortant influenza virus of embodiment 26, wherein the amino acid at the position corresponding to position 95 is altered to be lysine (K). |
| 28 | The reassortant influenza virus of embodiment 26, wherein the amino acid at the position corresponding to position 143 is altered to be alanine (A). |
| 29 | The reassortant influenza virus of embodiment 26, wherein the amino acid at the position corresponding to position 144 is altered to be phenylalanine (F). |
| 30 | The reassortant influenza virus of embodiment 26, wherein the amino acid at the position corresponding to position 218 is altered to be isoleucine (I). |
| 31 | The reassortant influenza virus of embodiment 26, wherein the amino acids at positions corresponding to each of positions 95, 143, 144, and 218 of the M1 protein of influenza strain MDV-A are altered. |
| 32 | The reassortant influenza virus of embodiment 26, wherein the replication capacity of the reassortant influenza virus is increased at least 2-fold relative to the same reassortant influenza virus in the absence of the alteration. |
| 33 | The reassortant influenza virus of embodiment 26, wherein the replication capacity of the reassortant influenza virus is increased at least 4-fold relative to the same reassortant influenza virus in the absence of the alteration. |
| 34 | The reassortant influenza virus of embodiment 26, wherein the replication capacity of the reassortant influenza virus is increased at least 8-fold relative to the same reassortant influenza virus in the absence of the alteration. |
| 35 | The reassortant influenza virus of embodiment 26, wherein the replication capacity of the reassortant influenza virus is increased at least 10-fold relative to the same reassortant influenza virus in the absence of the alteration. |
| 36 | The reassortant influenza virus of embodiment 26, wherein the reassortant influenza virus grows to a titer of at least about 7.5 log10 PFU/ml in embryonated eggs. |

TABLE 1-continued

| Specific embodiments | |
|---|---|
| 37 | The reassortant influenza virus of embodiment 26, wherein the reassortant influenza virus grows to a titer of at least about 8 log10 PFU/ml in embryonated eggs. |
| 38 | The reassortant influenza virus of embodiment 26, wherein the reassortant influenza virus grows to a titer of at least about 8.5 log10 PFU/ml in embryonated eggs. |
| 39 | The reassortant influenza virus of embodiment 26, wherein the reassortant influenza virus grows to a titer of at least about 9 log10 PFU/ml in embryonated eggs. |
| 40 | An immunogenic composition comprising the reassortant influenza virus of any of embodiments 26 to 39. |
| 41 | An influenza vaccine comprising the reassortant influenza virus of any of embodiments 26 to 39. |
| 42 | A live, cold-adapted, temperature-sensitive, attenuated influenza vaccine comprising the reassortant influenza virus of any of embodiments 26 to 39. |
| 43 | The reassortant influenza virus of any of embodiments 26 to 39, wherein the reassortant influenza virus is cold-adapted, temperature sensitive, or attenuated. |
| 44 | A reassortant influenza virus, comprising genomic segments 1, 2, 3, 5, and 8 from influenza strain MDV-A, genomic segment 7 from influenza strain A/Puerto Rico/8/34 (A/PR/8/34), and genomic segments 4 and 6 from an influenza strain. |
| 45 | The reassortant influenza virus of embodiment 44, wherein the reassortant influenza virus grows to a titer of at least about 7.5 log10 PFU/ml in embryonated eggs. |
| 46 | The reassortant influenza virus of embodiment 44, wherein the reassortant influenza virus grows to a titer of at least about 8 log10 PFU/ml in embryonated eggs. |
| 47 | The reassortant influenza virus of embodiment 44, wherein the reassortant influenza virus grows to a titer of at least about 8.5 log10 PFU/ml in embryonated eggs. |
| 48 | The reassortant influenza virus of embodiment 44, wherein the reassortant influenza virus grows to a titer of at least about 9 log10 PFU/ml in embryonated eggs. |
| 49 | An immunogenic composition comprising the reassortant influenza virus of embodiment 44. |
| 50 | An influenza vaccine comprising the reassortant influenza virus of embodiment 44. |
| 51 | A live, cold-adapted, temperature-sensitive, attenuated influenza vaccine comprising the reassortant influenza virus of embodiment 44. |
| 52 | An expression vector comprising a nucleic acid sequence operably linked to a pol I promoter, wherein the nucleic acid sequence encodes an influenza M1 protein comprising lysine (K) at position 95, alanine (A) at position 143, phenylalanine (F) at position 144, or isoleucine (I) at position 218, wherein the positions correspond to the M1 protein of influenza strain MDV-A, with the proviso that the sequence does not encode a wild-type M1 protein of influenza strain A/PR/8/34. |
| 53 | The expression vector of embodiment 52, wherein the M1 protein comprises lysine (K) at position 95, alanine (A) at position 143, phenylalanine (F) at position 144, and isoleucine (I) at position 218. |
| 54 | An isolated negative sense RNA expressed from the expression vector of embodiment 52 or 53. |
| 55 | An influenza M1 protein comprising lysine (K) at position 95, alanine (A) at position 143, phenylalanine (F) at position 144, or isoleucine (I) at position 218, wherein the positions correspond to the M1 protein of influenza strain MDV-A, with the proviso that the protein is not a wild-type M1 protein of influenza strain A/PR/8/34. |
| 56 | The influenza M1 protein of embodiment 55, comprising lysine (K) at position 95, alanine (A) at position 143, phenylalanine (F) at position 144, and isoleucine (I) at position 218. |

7. EXAMPLES

The following examples serve merely to illustrate the invention and are not intended to limit the invention in any way. Examples 1 and 2, below, demonstrate the identification and characterization of M1 amino acids that affect influenza virus replication.

7.1 Example 1

Identification of M1 Amino Acids that Affect Influenza Virus Replication Capacity This example describes identification of amino acid residues in influenza viral protein M1 that affect replication capacity in embryonated hens' eggs. Previous studies had identified a correlation between M gene genotype and increased viral replication capacity. See Klimov et al., 1991, *Virus Res.* 19:105-114. For example, influenza A strain A/PR/8/34 replicates to a titer ($1\times10^{8.76}$ PFU/ml) more than 10-fold greater than strain MDV-A ($1\times10^{7.35}$ PFU/ml) in embryonated hens' eggs. See FIG. 1.

Accordingly, the sequences of A/PR/8/34 and MDV-A M1 and M2 proteins were aligned and compared to identify amino acids that differ between the two strains. The sequence comparison identified six amino acid differences in the M1 protein (see FIG. 2) and 12 amino acid differences in the M2 protein (data not shown).

7.2 Example 2

Replication Capcity of Recombinant and/or Reassortant Influenza Virus Comprising M1 Mutations This example describes experiments to identify and characterize the effects of the variability in the M1 protein on influenza virus replication capacity. Methods for making reassortant influenza viruses, titering influenza viruses, infecting hens' eggs with influenza viruses, and rescue of influenza viruses from vectors are described, for example, in U.S. Patent Application Publication Nos. US20050158342, US20040029251, and US20050266026, and in Hoffman et al., 2002, *Proc. Nat. Acad. Sci. USA* 99:11411-6; Jin et al., 2003, *Virology* 306:18-24; and in Chen et al., 2006, *Virology* 345:416-23, each of which is hereby incorporated by reference.

Site directed mutagenesis of single amino acids and combinations of amino acids was performed to identify the effects of these amino acid differences on viral replication capacity of a cold adapted, temperature sensitive, attenuated A/Wyoming/3/03 strain. This strain was made from a 6:2 reassortant using the backbone of MDV-A and the HA and NA encoding segments from A/Wyoming/3/03, and is referred to herein as ca at ts A/Wyoming/3/03.

In these experiments, the amino acids at positions 41, 95, 116, 143, 144, 218 and various combinations thereof were mutated from the amino acid found in the A/Wyoming/3/03 M1 protein to the amino acid found in the A/PR/8/34 M1 protein. For controls, the ca at ts A/Wyoming/3/03 6:2 reassortant virus, a 5:3 reassortant virus containing the MDV-A backbone except for the M segment and M, HA and NA from A/Wyoming/3/03, and a 5:3 reassortant containing the MDV-A backbone except for the M segment, the M segment from A/PR/8/34, and HA and NA from A/Wyoming/3/03 were used. These various reassortant viruses were used to infect hens' eggs using conventional techniques and titered with a plaque assay on MDCK cells. Results of these experiments are presented in FIG. 3.

As shown in FIG. 3, the ca at ts A/Wyoming/3/03 reassortant virus exhibited the lowest titer of the reassortant viruses, while the 5:3 ca at ts A/Wyoming/3/03 with an M gene from A/PR/8/34 reassortant virus exhibited the highest titer. As also shown in FIG. 3, mutations at positions 95, 143, 144, and 218 also affected titer of replication. Changing the MDV-A M1 residue 95 from arginine to lysine slightly increased replication capacity; changing the MDV-A M1 residue 218 from valine to threonine slightly increased replication capacity; changing the MDV-A M1 residues 143 and 144 from valine and leucine to alanine and phenylalanine, respectively, slightly lowered replication capacity; changing the MDV-A M1 residues 143, 144, and 218 from valine, leucine, and valine to alanine, phenylalanine, and threonine, respectively, slightly increased replication capacity; and changing the MDV-A M1 residues 95, 143, 144, and 218 from arginine, valine, leucine, and valine to lysine, alanine, phenylalanine, and threonine, respectively, greatly increased replication capacity.

To confirm these effects, additional site-directed mutants were constructed altering the residues of the A/PR/8/34 M1 protein to those found in the MDV-A M1 protein. Vectors encoding these M gene mutants were used to produce 5:3 reassortant viruses with the MDV-A backbone, the ca A/Wyoming/3/03 HA and NA, and the appropriately modified A/PR/8/34 M gene. The various reassortant viruses were introduced into hens' eggs and titered by plaque assay on MDCK cells as described above. Viral titers obtained from these site-directed mutants are shown as FIG. 4.

As shown in FIG. 4, altering any of positions 65, 143, 144, or 218 from the amino acid found in A/PR/8/34 to the amino acid found in MDV-A resulted in reduced viral replication capacity in hens' eggs. The smallest reduction in replication capacity was observed for the single change of position 218 from threonine to valine, while the greatest reduction was observed for the double change of positions 143 and 144 from alanine and phenylalanine to valine and leucine, respectively.

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference.

The invention claimed is:

1. A method for increasing the replication capacity of an influenza virus strain MDV-A, comprising altering the amino acid at position 95 of the M1 protein of influenza virus strain MDV-A to lysine (K) and not altering the amino acids at positions 143, 144 and 218, wherein the amino acid at position 143 is valine, the amino acid at position 144 is leucine and the amino acid at position 218 is valine, thereby increasing the replication capacity of the influenza virus.

2. The method of claim 1, wherein the influenza virus grows to a titer of at least 7.5 $\log_{10}$ PFU/ml in embryonated eggs.

* * * * *